(12) United States Patent
Gerardi et al.

(10) Patent No.: US 11,793,230 B2
(45) Date of Patent: Oct. 24, 2023

(54) ORAL PRODUCTS WITH IMPROVED BINDING OF ACTIVE INGREDIENTS

(71) Applicant: NICOVENTURES TRADING LIMITED, London (GB)

(72) Inventors: Anthony Richard Gerardi, Winston-Salem, NC (US); Dwayne William Beeson, Kernersville, NC (US); Ronald K. Hutchens, East Bend, NC (US); Christopher Keller, Advance, NC (US); Thomas H. Poole, Winston-Salem, NC (US); Andries Don Sebastian, Winston-Salem, NC (US); Frank Kelley St. Charles, Bowling Green, KY (US)

(73) Assignee: NICOVENTURES TRADING LIMITED, London (GB)

( * ) Notice: Subject to any disclaimer, the term of this patent is extended or adjusted under 35 U.S.C. 154(b) by 584 days.

(21) Appl. No.: 16/707,602

(22) Filed: Dec. 9, 2019

(65) Prior Publication Data

US 2021/0169124 A1    Jun. 10, 2021

(51) Int. Cl.
*A24B 15/28* (2006.01)
*A24B 13/00* (2006.01)
(Continued)

(52) U.S. Cl.
CPC ............ *A24B 13/00* (2013.01); *A24B 15/281* (2013.01); *A24B 15/301* (2013.01);
(Continued)

(58) Field of Classification Search
None
See application file for complete search history.

(56) References Cited

U.S. PATENT DOCUMENTS

| 3,339,558 A | 9/1967 | Waterbury |
| 3,390,686 A | 7/1968 | Irby et al. |

(Continued)

FOREIGN PATENT DOCUMENTS

| AU | 2004/275 843 | 4/2008 |
| CA | 3042133 | 5/2018 |

(Continued)

OTHER PUBLICATIONS

Robichaud Meagan et al., "Tobacco companies introduce 'tobacco free' nicotine pouches", *Tob Control 2019*, Nov. 21, 2019, 1-2, National Library of Medicine, doi:10.1136/tobaccocontrol-2019-055321.

(Continued)

*Primary Examiner* — Eric Yaary
(74) *Attorney, Agent, or Firm* — Womble Bond Dickinson (US) LLP

(57) ABSTRACT

The disclosure provides products configured for oral use, the products including compositions comprising a filler component including negatively charged groups and an active ingredient including positively charged groups. The active ingredient can be retained by the filler component at least in part through bonding between the negatively charged groups and the positively charged groups such that active ingredient may be release from the product when positioned within an oral cavity of a consumer.

16 Claims, 1 Drawing Sheet

(51) Int. Cl.
*A24B 15/30* (2006.01)
*A24B 15/32* (2006.01)
*A24B 15/34* (2006.01)
*A24B 15/40* (2006.01)

(52) U.S. Cl.
CPC .......... *A24B 15/303* (2013.01); *A24B 15/308* (2013.01); *A24B 15/32* (2013.01); *A24B 15/34* (2013.01); *A24B 15/403* (2013.01)

(56) References Cited

U.S. PATENT DOCUMENTS

| | | |
|---|---|---|
| 3,550,598 A | 12/1970 | McGlumphy et al. |
| 3,685,521 A | 8/1972 | Dock |
| 3,916,914 A | 11/1975 | Brooks et al. |
| 4,241,093 A | 12/1980 | Farag et al. |
| 4,737,323 A | 4/1988 | Martin et al. |
| 4,889,144 A | 12/1989 | Tateno et al. |
| 4,997,654 A | 3/1991 | Corsello et al. |
| 5,004,595 A | 4/1991 | Cherukuri et al. |
| 5,223,185 A | 6/1993 | Takei et al. |
| 5,292,528 A | 3/1994 | Mori et al. |
| 5,387,093 A | 2/1995 | Takei et al. |
| 5,387,416 A | 2/1995 | White et al. |
| 5,417,229 A | 5/1995 | Summers et al. |
| 5,472,002 A | 12/1995 | Covarrubias |
| 5,525,351 A | 6/1996 | Dam |
| 5,690,990 A | 11/1997 | Bonner |
| 5,759,599 A | 6/1998 | Wampler et al. |
| 5,811,126 A | 9/1998 | Krishnamurthy |
| 5,882,680 A | 3/1999 | Suzuki et al. |
| 6,039,901 A | 3/2000 | Soper et al. |
| 6,045,835 A | 4/2000 | Soper et al. |
| 6,056,992 A | 5/2000 | Lew |
| 6,060,078 A | 5/2000 | Lee |
| 6,106,875 A | 8/2000 | Soper et al. |
| 6,117,455 A | 9/2000 | Takada et al. |
| 6,138,683 A | 10/2000 | Hersh et al. |
| 6,261,589 B1 | 7/2001 | Pearson et al. |
| 6,325,859 B1 | 12/2001 | DeRoos et al. |
| 6,482,433 B1 | 11/2002 | DeRoos et al. |
| 6,596,298 B2 | 7/2003 | Leung et al. |
| 6,612,429 B2 | 9/2003 | Dennen |
| 6,631,722 B2 | 10/2003 | MacAdam et al. |
| 6,719,933 B2 | 4/2004 | Nakamura et al. |
| 6,845,777 B2 | 1/2005 | Pera |
| 6,929,814 B2 | 8/2005 | Bouwmeesters et al. |
| 6,949,256 B2 | 9/2005 | Fonkwe et al. |
| 6,958,143 B2 | 10/2005 | Choi et al. |
| 7,032,601 B2 | 4/2006 | Atchley et al. |
| 7,056,541 B1 | 6/2006 | Stahl et al. |
| 7,067,150 B2 | 6/2006 | Farber et al. |
| 7,115,085 B2 | 10/2006 | Deal |
| 7,494,669 B2 | 2/2009 | Ni et al. |
| 7,507,427 B2 | 3/2009 | Andersen et al. |
| 7,531,192 B2 | 5/2009 | Farber et al. |
| 7,810,507 B2 | 10/2010 | Dube et al. |
| 7,833,555 B2 | 11/2010 | Andersen et al. |
| 7,861,728 B2 | 1/2011 | Holton, Jr. et al. |
| 7,900,637 B2 | 3/2011 | Fagerstrom et al. |
| 7,946,295 B2 | 5/2011 | Brinkley et al. |
| 7,950,399 B2 | 5/2011 | Winterson et al. |
| 8,069,861 B2 | 12/2011 | Sinclair |
| 8,124,147 B2 | 2/2012 | Cheng et al. |
| 8,293,295 B2 | 10/2012 | Andersen et al. |
| 8,336,557 B2 | 12/2012 | Kumar et al. |
| 8,343,532 B2 | 1/2013 | Dam et al. |
| 8,424,541 B2 | 4/2013 | Crawford et al. |
| 8,469,036 B2 | 6/2013 | Williams et al. |
| 8,469,037 B2 | 6/2013 | Liu et al. |
| 8,529,875 B2 | 9/2013 | Andersen |
| 8,529,914 B2 | 9/2013 | Fuisz et al. |
| 8,545,870 B2 | 10/2013 | Dupinay et al. |
| 8,591,967 B2 | 11/2013 | Andersen et al. |
| 8,613,285 B2 | 12/2013 | Fuisz |
| 8,627,828 B2 | 1/2014 | Strickland et al. |
| 8,642,016 B2 | 2/2014 | Chau et al. |
| 8,714,163 B2 | 5/2014 | Kumar et al. |
| 8,741,348 B2 | 6/2014 | Hansson et al. |
| 8,747,562 B2 | 6/2014 | Mishra et al. |
| 8,828,361 B2 | 9/2014 | Anderson |
| 8,833,378 B2 | 9/2014 | Axelsson et al. |
| 8,846,075 B2 | 9/2014 | Johnson et al. |
| 8,858,984 B2 | 10/2014 | Dam et al. |
| 8,863,755 B2 | 10/2014 | Zhuang et al. |
| 8,871,243 B2 | 10/2014 | Fankhauser et al. |
| 8,931,493 B2 | 1/2015 | Sebastian et al. |
| 8,945,593 B2 | 2/2015 | LoCoco et al. |
| 8,978,661 B2 | 3/2015 | Atchley et al. |
| 8,992,974 B2 | 3/2015 | McCarty |
| 9,027,567 B2 | 5/2015 | Gee et al. |
| 9,039,839 B2 | 5/2015 | Beeson et al. |
| 9,044,035 B2 | 6/2015 | Jackson et al. |
| 9,084,439 B2 | 7/2015 | Holton, Jr. |
| 9,155,321 B2 | 10/2015 | Cantrell et al. |
| 9,155,772 B2 | 10/2015 | Gao et al. |
| 9,161,567 B2 | 10/2015 | Shikata et al. |
| 9,161,908 B2 | 10/2015 | Nilsson |
| 9,167,835 B2 | 10/2015 | Sengupta et al. |
| 9,185,931 B2 | 11/2015 | Gao et al. |
| 9,204,667 B2 | 12/2015 | Cantrell et al. |
| 9,237,768 B2 | 1/2016 | Carroll et al. |
| 9,358,296 B2 | 6/2016 | McCarty |
| 9,372,033 B2 | 6/2016 | Ramm-Schmidt et al. |
| 9,375,033 B2 | 6/2016 | Lampe et al. |
| 9,386,800 B2 | 7/2016 | Sebastian et al. |
| 9,402,414 B2 | 8/2016 | Griscik et al. |
| 9,402,809 B2 | 8/2016 | Axelsson et al. |
| 9,402,810 B2 | 8/2016 | Nilsson |
| 9,414,624 B2 | 8/2016 | Carroll et al. |
| 9,420,825 B2 | 8/2016 | Beeson et al. |
| 9,468,233 B2 | 10/2016 | Macko et al. |
| 9,474,303 B2 | 10/2016 | Holton, Jr. |
| 9,521,864 B2 | 12/2016 | Gao et al. |
| 9,565,867 B2 | 2/2017 | Wittorff et al. |
| 9,629,392 B2 | 4/2017 | Holton, Jr. |
| 9,675,102 B2 | 6/2017 | Hunt et al. |
| 9,763,928 B2 | 9/2017 | Duggins et al. |
| 9,775,376 B2 | 10/2017 | Cantrell et al. |
| 9,801,409 B1 | 10/2017 | Smith |
| 9,848,634 B2 | 12/2017 | Fuisz |
| 9,854,830 B2 | 1/2018 | Gao et al. |
| 9,884,015 B2 | 2/2018 | Gao et al. |
| 9,907,748 B2 | 3/2018 | Borschke et al. |
| 9,925,145 B2 | 3/2018 | Hubinette et al. |
| 9,930,909 B2 | 4/2018 | Gao et al. |
| 9,950,858 B2 | 4/2018 | Byrd et al. |
| 9,999,243 B2 | 6/2018 | Gao et al. |
| 10,039,309 B2 | 8/2018 | Carroll et al. |
| 10,045,976 B2 | 8/2018 | Fusco et al. |
| 10,092,715 B2 | 10/2018 | Axelsson et al. |
| 10,130,120 B2 | 11/2018 | Mishra et al. |
| 10,143,230 B2 | 12/2018 | Mishra et al. |
| 10,149,850 B2 | 12/2018 | Mishra et al. |
| 10,172,810 B2 | 1/2019 | McCarty |
| 10,244,786 B2 | 4/2019 | Gao et al. |
| 10,328,023 B2 | 6/2019 | Romanoschi et al. |
| 10,334,873 B2 | 7/2019 | Mishra et al. |
| 10,349,672 B2 | 7/2019 | Gao et al. |
| 10,357,054 B2 | 7/2019 | Marshall et al. |
| 10,369,182 B2 | 8/2019 | Cohen |
| 10,375,984 B2 | 8/2019 | Hernandez Garcia et al. |
| 10,390,557 B2 | 8/2019 | Börjesson et al. |
| 10,426,726 B2 | 10/2019 | Neergaard |
| 10,463,070 B2 | 11/2019 | Carroll et al. |
| 10,517,322 B1 | 12/2019 | Lee |
| 10,532,046 B2 | 1/2020 | Rogers et al. |
| 10,543,205 B2 | 1/2020 | Wittorff et al. |
| 10,881,132 B2 | 1/2021 | Mua et al. |
| 2001/0045215 A1 | 11/2001 | Meyer et al. |
| 2002/0006919 A1 | 1/2002 | Thosar et al. |
| 2003/0224090 A1 | 4/2003 | Pearce et al. |
| 2003/0118628 A1 | 6/2003 | Tutuncu et al. |
| 2004/0118422 A1 | 6/2004 | Lundin et al. |

(56) References Cited

U.S. PATENT DOCUMENTS

| | | |
|---|---|---|
| 2004/0191322 A1 | 9/2004 | Hansson |
| 2004/0224020 A1 | 11/2004 | Schoenhard |
| 2004/0261807 A1 | 12/2004 | Dube et al. |
| 2005/0061339 A1 | 3/2005 | Hansson et al. |
| 2005/0123601 A1 | 6/2005 | Mane et al. |
| 2005/0196437 A1 | 9/2005 | Bednarz et al. |
| 2005/0244521 A1 | 11/2005 | Strickland et al. |
| 2005/0249676 A1 | 11/2005 | Scott et al. |
| 2006/0130861 A1 | 6/2006 | Luan et al. |
| 2006/0144412 A1 | 7/2006 | Mishra et al. |
| 2006/0174901 A1 | 8/2006 | Karles et al. |
| 2006/0191548 A1 | 8/2006 | Strickland et al. |
| 2006/0263414 A1 | 11/2006 | Pan et al. |
| 2006/0272663 A1 | 12/2006 | Dube et al. |
| 2007/0012327 A1 | 1/2007 | Karles et al. |
| 2007/0031539 A1 | 2/2007 | Calton |
| 2007/0062549 A1 | 3/2007 | Holton, Jr. et al. |
| 2007/0082101 A1 | 4/2007 | Weismuller |
| 2007/0092554 A1 | 4/2007 | Lindberg et al. |
| 2007/0095357 A1 | 5/2007 | Besso et al. |
| 2007/0148292 A1 | 6/2007 | Royo et al. |
| 2007/0184093 A1 | 8/2007 | Hang |
| 2007/0186941 A1 | 8/2007 | Holton et al. |
| 2007/0261707 A1* | 11/2007 | Winterson ............ A24B 13/00 131/357 |
| 2007/0269386 A1 | 11/2007 | Steen et al. |
| 2008/0029110 A1 | 2/2008 | Dube et al. |
| 2008/0029117 A1 | 2/2008 | Mua et al. |
| 2008/0081071 A1 | 4/2008 | Sanghvi et al. |
| 2008/0142025 A1 | 6/2008 | Sinclair |
| 2008/0166395 A1 | 7/2008 | Roush |
| 2008/0202536 A1 | 8/2008 | Torrence et al. |
| 2008/0233245 A1 | 9/2008 | White et al. |
| 2008/0308115 A1 | 12/2008 | Zimmermann |
| 2008/0317911 A1 | 12/2008 | Schleef et al. |
| 2009/0023819 A1 | 1/2009 | Axelsson |
| 2009/0025739 A1 | 1/2009 | Brinkley et al. |
| 2009/0053388 A1 | 2/2009 | Powers et al. |
| 2009/0065013 A1 | 3/2009 | Essen et al. |
| 2009/0095313 A1 | 4/2009 | Fuisz |
| 2009/0142443 A1 | 6/2009 | Robinson et al. |
| 2009/0253754 A1 | 10/2009 | Selmin et al. |
| 2009/0263476 A1 | 10/2009 | Jobdevairakkam et al. |
| 2009/0301504 A1 | 12/2009 | Worthen et al. |
| 2010/0004294 A1 | 1/2010 | Axelsson et al. |
| 2010/0018541 A1 | 1/2010 | Gerardi et al. |
| 2010/0061940 A1 | 3/2010 | Axelsson et al. |
| 2010/0126520 A1 | 5/2010 | Clayton |
| 2010/0187143 A1 | 7/2010 | Essen et al. |
| 2010/0218779 A1 | 9/2010 | Zhuang et al. |
| 2010/0260690 A1 | 10/2010 | Kristensen et al. |
| 2010/0291245 A1 | 11/2010 | Gao et al. |
| 2010/0294292 A1 | 11/2010 | Hodin et al. |
| 2010/0300464 A1 | 12/2010 | Gee et al. |
| 2010/0326454 A1 | 12/2010 | Fuisz |
| 2011/0083680 A1 | 4/2011 | Mishra et al. |
| 2011/0083681 A1 | 4/2011 | Sengupta et al. |
| 2011/0104218 A1 | 4/2011 | Mishra et al. |
| 2011/0129517 A1 | 6/2011 | Rudolph et al. |
| 2011/0139164 A1 | 6/2011 | Mua et al. |
| 2011/0139166 A1 | 6/2011 | Luzenberg, Jr. |
| 2011/0220130 A1 | 9/2011 | Mua et al. |
| 2011/0223297 A1 | 9/2011 | Corkery et al. |
| 2011/0232662 A1 | 9/2011 | Liu et al. |
| 2011/0236536 A1 | 9/2011 | Mongia |
| 2011/0247640 A1 | 10/2011 | Beeson et al. |
| 2011/0268809 A1 | 11/2011 | Brinkley et al. |
| 2011/0274628 A1 | 11/2011 | Borschke |
| 2011/0288132 A1 | 11/2011 | Lindberg |
| 2011/0303232 A1 | 12/2011 | Williams |
| 2012/0031415 A1 | 2/2012 | Essen et al. |
| 2012/0031416 A1 | 2/2012 | Atchley et al. |
| 2012/0037175 A1 | 2/2012 | Cantrell et al. |
| 2012/0039981 A1 | 2/2012 | Pedersen et al. |
| 2012/0103353 A1 | 5/2012 | Sebastian et al. |
| 2012/0128734 A1 | 5/2012 | Hubinette et al. |
| 2012/0138074 A1 | 6/2012 | Cantrell et al. |
| 2012/0138075 A1 | 6/2012 | Jespersen et al. |
| 2012/0177818 A1 | 7/2012 | Trivedi et al. |
| 2013/0005831 A1 | 1/2013 | Rajewski et al. |
| 2013/0074856 A1 | 3/2013 | Holton, Jr. |
| 2013/0078307 A1 | 3/2013 | Holton, Jr. et al. |
| 2013/0098377 A1 | 4/2013 | Borschke et al. |
| 2013/0118512 A1 | 5/2013 | Jackson et al. |
| 2013/0152953 A1 | 6/2013 | Mua et al. |
| 2013/0177646 A1 | 7/2013 | Hugerth et al. |
| 2013/0206115 A1 | 8/2013 | Kragh |
| 2013/0206150 A1 | 8/2013 | Duggins et al. |
| 2013/0206153 A1 | 8/2013 | Beeson et al. |
| 2013/0209540 A1 | 8/2013 | Duggins et al. |
| 2013/0251779 A1 | 9/2013 | Svandal et al. |
| 2013/0263870 A1 | 10/2013 | Cantrell et al. |
| 2013/0276801 A1 | 10/2013 | Byrd, Jr. et al. |
| 2013/0312774 A1 | 11/2013 | Holton, Jr. |
| 2013/0330379 A1 | 12/2013 | Ylipertula et al. |
| 2013/0330417 A1 | 12/2013 | Dong et al. |
| 2013/0340773 A1 | 12/2013 | Sebastian et al. |
| 2014/0130813 A1 | 5/2014 | Strehle |
| 2014/0154301 A1 | 6/2014 | Chau et al. |
| 2014/0234392 A1 | 8/2014 | Hansson et al. |
| 2014/0255452 A1 | 9/2014 | Reddick et al. |
| 2014/0261485 A1 | 9/2014 | Kobai et al. |
| 2014/0271791 A1 | 9/2014 | Mishra et al. |
| 2014/0271946 A1 | 9/2014 | Kobai et al. |
| 2014/0332013 A1 | 11/2014 | Gao et al. |
| 2015/0068544 A1 | 3/2015 | Moldoveanu et al. |
| 2015/0068545 A1 | 3/2015 | Moldoveanu et al. |
| 2015/0071972 A1 | 3/2015 | Holton, Jr. et al. |
| 2015/0096573 A1 | 4/2015 | Gao et al. |
| 2015/0096574 A1 | 4/2015 | Gao et al. |
| 2015/0096576 A1 | 4/2015 | Gao et al. |
| 2015/0098996 A1 | 4/2015 | Gao et al. |
| 2015/0101627 A1 | 4/2015 | Marshall et al. |
| 2015/0230515 A1 | 8/2015 | Lampe et al. |
| 2015/0231070 A1 | 8/2015 | Huang |
| 2015/0296868 A1 | 10/2015 | Sutton |
| 2015/0368368 A1 | 12/2015 | Retsina et al. |
| 2016/0000140 A1 | 1/2016 | Sebastian et al. |
| 2016/0038552 A1 | 2/2016 | Bredesen et al. |
| 2016/0073657 A1 | 3/2016 | Campomanes et al. |
| 2016/0073676 A1 | 3/2016 | Cantrell et al. |
| 2016/0073689 A1 | 3/2016 | Sebastian et al. |
| 2016/0157515 A1 | 6/2016 | Chapman et al. |
| 2016/0165953 A1 | 6/2016 | Goode, Jr. |
| 2016/0166543 A1 | 6/2016 | Joshi et al. |
| 2016/0186377 A1 | 6/2016 | Haldane et al. |
| 2016/0192703 A1 | 7/2016 | Sebastian et al. |
| 2016/0279056 A1 | 9/2016 | Zhao et al. |
| 2016/0303042 A1 | 10/2016 | Yoshimura et al. |
| 2016/0324777 A1 | 11/2016 | Victor et al. |
| 2017/0007594 A1 | 1/2017 | Borschke |
| 2017/0028672 A1 | 2/2017 | Lim et al. |
| 2017/0099868 A1 | 4/2017 | Gao et al. |
| 2017/0157106 A1 | 6/2017 | Rogers et al. |
| 2017/0164651 A1 | 6/2017 | Mua et al. |
| 2017/0165252 A1 | 6/2017 | Mua et al. |
| 2017/0172995 A1 | 6/2017 | Repaka et al. |
| 2017/0209380 A1* | 7/2017 | Ognibene ............ A61K 9/2027 |
| 2017/0216213 A1* | 8/2017 | Ognibene ............ A61K 9/2054 |
| 2017/0239336 A1 | 8/2017 | Zanetti |
| 2017/0258918 A1 | 9/2017 | Rifkin et al. |
| 2017/0258978 A1 | 9/2017 | Bartlett et al. |
| 2017/0280764 A1 | 10/2017 | Sahlen et al. |
| 2017/0312261 A1 | 11/2017 | Changoer et al. |
| 2017/0318844 A1 | 11/2017 | Gordon |
| 2017/0318858 A1 | 11/2017 | Hodin et al. |
| 2018/0044856 A1 | 2/2018 | Dhumpa et al. |
| 2018/0049979 A1 | 2/2018 | Zhao et al. |
| 2018/0051002 A1 | 2/2018 | Dull et al. |
| 2018/0140007 A1 | 5/2018 | Aspgren et al. |
| 2018/0140521 A1 | 5/2018 | Geonnotti et al. |
| 2018/0140554 A1 | 5/2018 | Wittorff |
| 2018/0153211 A1 | 6/2018 | Persson |
| 2018/0235273 A1 | 8/2018 | Carroll et al. |

(56) References Cited

U.S. PATENT DOCUMENTS

| | | | |
|---|---|---|---|
| 2018/0255826 A1 | 9/2018 | Persson et al. | |
| 2018/0257801 A1 | 9/2018 | Persson | |
| 2018/0271112 A1 | 9/2018 | Barkalow et al. | |
| 2018/0338892 A1 | 11/2018 | Budde et al. | |
| 2019/0008766 A1 | 1/2019 | Favara et al. | |
| 2019/0037909 A1 | 2/2019 | Greenbaum et al. | |
| 2019/0083393 A1 | 3/2019 | Axelsson et al. | |
| 2019/0110514 A1 | 4/2019 | Vetter | |
| 2019/0124971 A1 | 5/2019 | Soffe et al. | |
| 2019/0174812 A1 | 6/2019 | Nielsen et al. | |
| 2019/0175581 A1 | 6/2019 | Nielsen et al. | |
| 2019/0246686 A1 | 8/2019 | Zhuang et al. | |
| 2019/0254337 A1 | 8/2019 | Bjoerkholm | |
| 2019/0255035 A1 | 8/2019 | Bruun | |
| 2019/0313689 A1 | 10/2019 | Beeson et al. | |
| 2019/0350862 A1 | 11/2019 | Wittorff | |
| 2020/0037638 A1 | 2/2020 | Faraci et al. | |
| 2020/0128870 A1 | 4/2020 | Hassler et al. | |
| 2020/0138706 A1 | 5/2020 | Rudraraju et al. | |
| 2020/0138783 A1 | 5/2020 | Rinaldi et al. | |
| 2020/0275689 A1 | 9/2020 | Lewerenz | |
| 2020/0297026 A1 | 9/2020 | Kannisto et al. | |
| 2020/0305496 A1 | 10/2020 | Gessesse | |
| 2020/0316012 A1 | 10/2020 | Schou | |
| 2020/0330423 A1 | 10/2020 | Brunn et al. | |
| 2020/0383372 A1 | 12/2020 | Stahl et al. | |
| 2020/0383373 A1 | 12/2020 | Stahl et al. | |
| 2020/0392051 A1 * | 12/2020 | Casalins Cuñado ... | A01G 31/00 |
| 2021/0023046 A1 * | 1/2021 | Bruun ................ | A61K 47/12 |
| 2021/0068446 A1 | 3/2021 | Keller et al. | |
| 2021/0198508 A1 * | 7/2021 | Ikegami ............. | C09D 11/14 |
| 2022/0225659 A1 | 7/2022 | Gessesse et al. | |
| 2022/0295858 A1 | 9/2022 | Holton, Jr. et al. | |

FOREIGN PATENT DOCUMENTS

| | | | |
|---|---|---|---|
| CA | 3040513 | 10/2020 | |
| CN | 103005680 | 4/2013 | |
| CN | 103263507 | 8/2013 | |
| CN | 103494324 | 1/2014 | |
| CN | 105192876 | 12/2015 | |
| CN | 105595404 | 5/2016 | |
| CN | 105916603 | 8/2016 | |
| CN | 105918603 | 9/2016 | |
| CN | 106805287 | 6/2017 | |
| CN | 108649170 | 10/2018 | |
| CN | 104770860 | 5/2020 | |
| DE | 19524197 | 9/1997 | |
| EP | 2177213 A1 | 4/2010 | |
| EP | 2417967 | 2/2012 | |
| EP | 2640204 | 9/2013 | |
| EP | 1951074 B1 | 7/2014 | |
| EP | 2804498 | 11/2014 | |
| EP | 2891408 | 7/2015 | |
| EP | 3087852 | 11/2016 | |
| GB | 2487808 | 8/2012 | |
| JP | 2004/161719 | 6/2004 | |
| SE | 1750488 | 10/2018 | |
| SE | 541198 C2 | 4/2019 | |
| WO | WO 96/31255 | 10/1996 | |
| WO | WO 97/012605 | 4/1997 | |
| WO | WO 00/013662 | 3/2000 | |
| WO | WO 02/080707 | 10/2002 | |
| WO | WO2003/039518 | 5/2003 | |
| WO | WO 03/053175 | 7/2003 | |
| WO | WO2004/000273 | 12/2003 | |
| WO | WO2004/056219 | 7/2004 | |
| WO | WO2004/056363 | 7/2004 | |
| WO | WO 2004/095959 | 11/2004 | |
| WO | WO 2005/046363 | 5/2005 | |
| WO | WO2005041699 | 5/2005 | |
| WO | WO 2005/063060 | 7/2005 | |
| WO | WO2006/000232 | 1/2006 | |
| WO | WO 2007/037962 | 4/2007 | |
| WO | WO 2007/053098 | 5/2007 | |
| WO | WO 2007/126361 | 11/2007 | |
| WO | WO2008/056135 | 5/2008 | |
| WO | WO 2008/103935 | 8/2008 | |
| WO | WO 2009/015142 | 1/2009 | |
| WO | WO2009/067734 | 6/2009 | |
| WO | WO2009/108769 | 9/2009 | |
| WO | WO 2010/125516 | 11/2010 | |
| WO | WO2010/0134025 | 11/2010 | |
| WO | WO 2010/139987 | 12/2010 | |
| WO | WO 2011/081725 | 7/2011 | |
| WO | WO 2011/117740 | 9/2011 | |
| WO | WO 2013/119760 | 8/2013 | |
| WO | WO 2013/119799 | 8/2013 | |
| WO | WO 2015/051308 | 4/2015 | |
| WO | WO 2015/067372 | 5/2015 | |
| WO | WO 2015/075745 | 5/2015 | |
| WO | WO 2015/117011 | 8/2015 | |
| WO | WO 2015/160842 | 10/2015 | |
| WO | WO 2015/193379 | 12/2015 | |
| WO | WO2016/067226 | 5/2016 | |
| WO | WO 2016/075371 | 5/2016 | |
| WO | WO2016/090075 | 6/2016 | |
| WO | WO2016/144376 | 9/2016 | |
| WO | WO2016/147186 | 9/2016 | |
| WO | WO 2016/164470 | 10/2016 | |
| WO | WO2018/009139 | 1/2018 | |
| WO | WO2018/029626 | 2/2018 | |
| WO | WO2018/197454 | 11/2018 | |
| WO | WO-2018197454 A1 * | 11/2018 | ............ A24B 13/00 |
| WO | WO2018/233782 | 12/2018 | |
| WO | WO 2019/005889 | 1/2019 | |
| WO | WO2019/036243 | 2/2019 | |
| WO | WO2019/094745 | 5/2019 | |
| WO | WO2019/115778 | 6/2019 | |
| WO | WO2019/135224 | 7/2019 | |
| WO | WO2019/140406 | 7/2019 | |
| WO | WO2019/219147 | 11/2019 | |
| WO | WO 2019/245639 | 12/2019 | |
| WO | WO2020/236798 | 11/2020 | |
| WO | WO 2021/086367 | 5/2021 | |

OTHER PUBLICATIONS

Ali Ashjaran et al: "Overview of bionanofabric from bacterial cellulose", The Journal of the Textile Institute, vol. 104, No. 2,Feb. 1, 2013, pp. 121-131.
Gennady Dvoryanchikov et al., "GABA, Its Receptors, and GABAergic Inhibition in Mouse Taste Buds" The Journal of Neuroscience, Apr. 13, 2011 • 31(15):5782-5791.
Qingqing Liu et al., "Food-Grade Nanoemulsions: Preparation, Stability and Application in Encapsulation of Bioactive Compounds" Molecules 2019, 24, 4242-4279.
Shit, Subhas et al., "Edible Polymers: Challenges and Opportunities", Journal of Polymers vol. 2014, Article ID 427259, 13 pages; http://dx.doi.org/10.1155/2014/427259.
Vieira, Melissa et al., "Natural-based plasticizers and biopolymer films: A review", European Polymer Journal 47, (2011), 254-263.
Acton et al., Chapter 3: Esterases from "Hydrolases-Advances in Research and Publication," 2003, p. 160.
Cash, M.J. et al., "Cellulose Derivatives," Imelson, Alan, Food Stabilisers, Thickeners and Gelling Agents, 2010, Blackwell Publishing Ltd., 1$^{st}$ Edition, p. 95-113.
Ester, Valerate, "Chemical Entities of Biological Interest," European Molecular Biology Laboratory, 2019, https://www.ebi.ac.uk/chebi/searchld.do?chebild=CHEBI:50871.
Fernandes et al., "Manufacture and Characterization of Mucoadhesive Buccal Films Based on Pectin and Gellan Gum Containing Triamcinolone Acetonide," *International Journal of Polymer Science*, vol. 2018, pp. 1-10.
Friedman et al., "Cinnamaldehyde Content in Foods Determined by Gas Chromatography-Mass Spectrometry," 2000, Journal of Agricultural and Food Chemistry, vol. 48, No. 11, pp. 5702-5709.
Guntert in Takeoka, et al., "Flavor Chemistry of Peppermint Oil (*Mentha piperita* L.)," Aroma Active Compounds in Foods ACS Symposium Series; American Chemical Society: Washington, DC 2001.

(56) References Cited

OTHER PUBLICATIONS

Lee et al., "Gums, Jellies and Pastilles," in Sugar Confectionery and Chocolate Manufacture, 1973, pp. 226-255.

Mohammaei et al: "Coefficient partition prediction of saturated monocarboxylic acids using the molecular descriptors", Journal of the Chilean Chemical Society, vol. 63, No. 3, 2018, pp. 4068-4071.

Nestor et al., "Role of Oxides of Nitrogen in Tobacco-Specific Nitrosamine Formation in Flue-Cured Tobacco" Beitrage Tabakforsch. Int., 20, 467-475 (2003).

Niesz, Krisztian, et al., "Sol-gel Synthesis of ordered mesoporous alumina," Chem. Commun., 2005, pp. 1986-1987.

Onal et al., "Some Physicochemical Properties Of The White Sepiolite Known As Pipestone From Kskisehir, Turkey," 2008, Clays and Clay Minerals, vol. 56, No. 5, pp. 511-519.

Perfetti, T. A. "Structural study of nicotine salts" Beitrage Tabakforschung Int., 12: 43-54 (1983).

Roton et al., "Factors Influencing the Formation of Tobacco-Specific Nitrosamines in French Air-Cured Tobaccos in Trials and at the Farm Level" Beitrage Tabakforsch. Int., 21, 305-320 (2005).

Staaf et al., "Formation of Tobacco-Specific Nitrosamines (TSNA) During Air-Curing: Conditions and Control" Beitrage Tabakforsch. Int., 21, 321-330 (2005).

Szel, et al., "Anti-irritant and anti-inflammatory effects of glycerol and xylitol in sodium lauryl sulphate-induced acute irritation," The Journal of European Academy of Dermatology and Venereology, vol. 29, Issue 12, Dec. 2015, 2333-2341.

Umashankar et al., Chewable Lozenges Formulation a Review, International Research Journal of Pharmacy, 2016, 7(4), 9-16.

V2 Cigs UK, "What is Synthetic Nicotine and is it safe?" Sep. 11, 2019, (https://www.buyv2cigs.co.uk/).

* cited by examiner

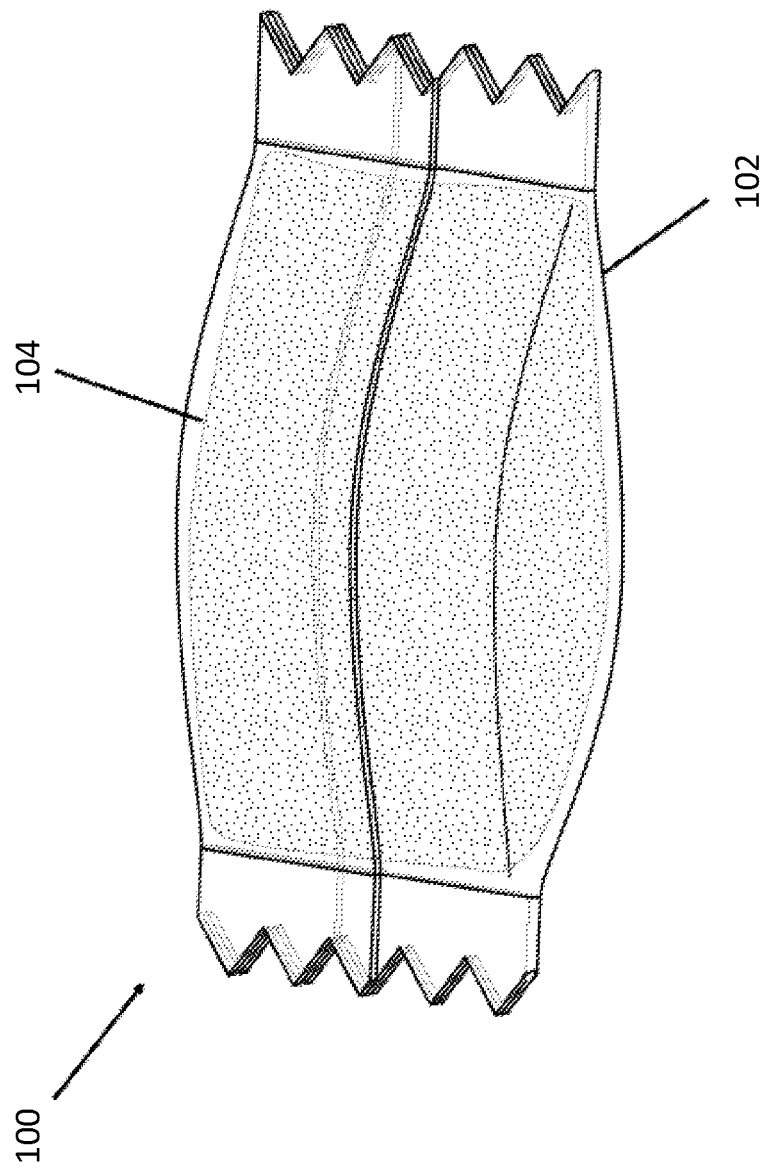

1

ORAL PRODUCTS WITH IMPROVED BINDING OF ACTIVE INGREDIENTS

FIELD OF THE DISCLOSURE

The present disclosure relates to flavored products intended for human use. The products are configured for oral use and deliver substances such as flavors and/or active ingredients during use. Such products may include tobacco or a product derived from tobacco, or may be tobacco-free alternatives.

BACKGROUND

Tobacco may be enjoyed in a so-called "smokeless" form. Particularly popular smokeless tobacco products are employed by inserting some form of processed tobacco or tobacco-containing formulation into the mouth of the user. Conventional formats for such smokeless tobacco products include moist snuff, snus, and chewing tobacco, which are typically formed almost entirely of particulate, granular, or shredded tobacco, and which are either portioned by the user or presented to the user in individual portions, such as in single-use pouches or sachets. Other traditional forms of smokeless products include compressed or agglomerated forms, such as plugs, tablets, or pellets. Alternative product formats, such as tobacco-containing gums and mixtures of tobacco with other plant materials, are also known. See for example, the types of smokeless tobacco formulations, ingredients, and processing methodologies set forth in U.S. Pat. No. 1,376,586 to Schwartz; U.S. Pat. No. 4,513,756 to Pittman et al.; U.S. Pat. No. 4,528,993 to Sensabaugh, Jr. et al.; U.S. Pat. No. 4,624,269 to Story et al.; U.S. Pat. No. 4,991,599 to Tibbetts; U.S. Pat. No. 4,987,907 to Townsend; U.S. Pat. No. 5,092,352 to Sprinkle, III et al.; U.S. Pat. No. 5,387,416 to White et al.; U.S. Pat. No. 6,668,839 to Williams; U.S. Pat. No. 6,834,654 to Williams; U.S. Pat. No. 6,953,040 to Atchley et al.; U.S. Pat. No. 7,032,601 to Atchley et al.; and U.S. Pat. No. 7,694,686 to Atchley et al.; US Pat. Pub. Nos. 2004/0020503 to Williams; 2005/0115580 to Quinter et al.; 2006/0191548 to Strickland et al.; 2007/0062549 to Holton, Jr. et al.; 2007/0186941 to Holton, Jr. et al.; 2007/0186942 to Strickland et al.; 2008/0029110 to Dube et al.; 2008/0029116 to Robinson et al.; 2008/0173317 to Robinson et al.; 2008/0209586 to Neilsen et al.; 2009/0065013 to Essen et al.; and 2010/0282267 to Atchley, as well as WO2004/095959 to Arnarp et al., each of which is incorporated herein by reference.

Smokeless tobacco product configurations that combine tobacco material with various binders and fillers have been proposed more recently, with example product formats including lozenges, pastilles, gels, extruded forms, and the like. See, for example, the types of products described in US Patent App. Pub. Nos. 2008/0196730 to Engstrom et al.; 2008/0305216 to Crawford et al.; 2009/0293889 to Kumar et al.; 2010/0291245 to Gao et al; 2011/0139164 to Mua et al.; 2012/0037175 to Cantrell et al.; 2012/0055494 to Hunt et al.; 2012/0138073 to Cantrell et al.; 2012/0138074 to Cantrell et al.; 2013/0074855 to Holton, Jr.; 2013/0074856 to Holton, Jr.; 2013/0152953 to Mua et al.; 2013/0274296 to Jackson et al.; 2015/0068545 to Moldoveanu et al.; 2015/0101627 to Marshall et al.; and 2015/0230515 to Lampe et al., each of which is incorporated herein by reference.

All-white snus portions are growing in popularity, and offer a discrete and aesthetically pleasing alternative to traditional snus. Such modern "white" pouched products may include a bleached tobacco or may be tobacco-free. Products of this type may suffer from certain drawbacks, such as poor product stability that could lead to discoloration of the product and/or undesirable organoleptic characteristics.

BRIEF SUMMARY

The present disclosure generally provides products configured for oral use. The products may be configured to impart a taste when used orally and, additionally or alternatively, may deliver active ingredients to a consumer, such as nicotine. The products and methods of the present disclosure in particular may provide for improved binding of materials including a positively charged group through binding with a component including a negatively charged group.

The disclosure includes, without limitations, the following embodiments.

Embodiment 1: An oral product comprising an active ingredient comprising a positively charged group and a filler comprising a negatively charged group, wherein the active ingredient is retained by the filler through bonding of the respective positively charged group and negatively charged group, wherein the active ingredient is configured for release when the product is present in an oral cavity.

Embodiment 2: The product of embodiment 1, wherein the active ingredient can be selected from the group consisting of a nicotine component, botanicals, stimulants, amino acids, vitamins, cannabinoids, nutraceuticals, and combinations thereof.

Embodiment 3: The product of any one of embodiments 1 to 2, wherein the active ingredient can comprise protonated nicotine.

Embodiment 4: The product of any one of embodiments 1 to 3, wherein the product further can comprise one or more flavoring agents.

Embodiment 5: The product of any one of embodiments 1 to 4, wherein the one or more flavoring agents can comprise a compound having a carbon-carbon double bond, a carbon-oxygen double bond, or both.

Embodiment 6: The product of any one of embodiments 1 to 5, wherein the one or more flavoring agents can comprise one or more aldehydes, ketones, esters, terpenes, terpenoids, trigeminal sensates, or a combination thereof.

Embodiment 7: The product of any one of embodiments 1 to 6, wherein the one or more flavoring agents can comprise one or more of ethyl vanillin, cinnamaldehyde, sabinene, limonene, gamma-terpinene, beta-farnesene, and citral.

Embodiment 8: The product of any one of embodiments 1 to 7, wherein filler can be in a particulate form.

Embodiment 9: The product of any one of embodiments 1 to 8, wherein the negatively charged group of the filler can comprise at least a carboxyl group.

Embodiment 10: The product of any one of embodiments 1 to 9, wherein the filler can be a cellulose material or cellulose derivative.

Embodiment 11: The product of any one of embodiments 1 to 10, wherein the filler can be microcrystalline cellulose.

Embodiment 12: The product of any one of embodiments 1 to 11, wherein the filler can be carboxylated microcrystalline cellulose.

Embodiment 13: The product of any one of embodiments 1 to 12, wherein the product can comprise no more than about 10% by weight of a tobacco material, excluding any nicotine component present, based on the total weight of the mixture.

Embodiment 14: The product of any one of embodiments 1 to 13, wherein at least the active ingredient and the filler can be combined as a mixture that is enclosed in a pouch to form a pouched product, the mixture optionally being in a free-flowing particulate form.

Embodiment 15: The product of any one of embodiments 1 to 14, wherein the product further can comprise one or more salts, one or more sweeteners, one or more binding agents, one or more humectants, one or more gums, a tobacco material, a buffer, or combinations thereof.

Embodiment 16: The product of any one of embodiments 1 to 15, wherein the positively charged group of the active ingredient can comprise at least one amine group.

Embodiment 17: A method for improving binding of an active ingredient in an oral product, the method comprising mixing an active ingredient comprising a positively charged group with a filler comprising a negatively charged group such that the active ingredient is retained by the filler though bonding between the respective positively charged group and negatively charged group, and such that the active ingredient that is so-retained is configured for release therefrom when the product is present in an oral cavity.

Embodiment 18: The method of embodiment 17, wherein the active ingredient can be selected from the group consisting of a nicotine component, botanicals, stimulants, amino acids, vitamins, cannabinoids, nutraceuticals, and combinations thereof.

Embodiment 19: The method of any one of embodiments 17 to 18, wherein the active ingredient can comprise protonated nicotine.

Embodiment 20: The method of any one of embodiments 17 to 19, wherein the negatively charged group of the filler can comprise at least one carboxyl group.

Embodiment 21: The method of any one of embodiments 17 to 20, wherein the positively charged group of the active ingredient can comprise at least one amine group.

Embodiment 22: The method of any one of embodiments 17 to 21, wherein the filler component can be a cellulose material or cellulose derivative.

Embodiment 23: The method of any one of embodiments 17 to 22, wherein the filler component can be microcrystalline cellulose.

Embodiment 24: The method of any one of embodiments 17 to 23, wherein the filler component can be carboxylated microcrystalline cellulose.

Embodiment 25: Use of charged groups for improving bonding of an active ingredient in an oral product by forming the oral product through mixing an active ingredient comprising a positively charged group with a filler comprising a negatively charged group such that the active ingredient is retained by the filler though bonding between the respective positively charged group and negatively charged group, and such that the active ingredient that is so-retained is configured for release therefrom when the product is present in an oral cavity.

These and other features, aspects, and advantages of the disclosure will be apparent from a reading of the following detailed description together with the accompanying drawings, which are briefly described below. The invention includes any combination of two, three, four, or more of the above-noted embodiments as well as combinations of any two, three, four, or more features or elements set forth in this disclosure, regardless of whether such features or elements are expressly combined in a specific embodiment description herein. This disclosure is intended to be read holistically such that any separable features or elements of the disclosed invention, in any of its various aspects and embodiments, should be viewed as intended to be combinable unless the context clearly dictates otherwise.

BRIEF DESCRIPTION OF THE DRAWING

Having thus described aspects of the disclosure in the foregoing general terms, reference will now be made to the accompanying drawing, which is not necessarily drawn to scale. The drawing is exemplary only, and should not be construed as limiting the disclosure.

The FIGURE is a perspective view of a pouched product according to an example embodiment of the present disclosure including a pouch or fleece at least partially filled with a composition for oral use.

DETAILED DESCRIPTION

The present disclosure provides compositions and products formed therefrom, the compositions and products particularly being configured for oral use. The compositions and products may incorporate one or more components that are effective for retaining a releasable component and then releasing the releasable component at a desired time, such as when in contact with an oral cavity. The components for retaining the releasable component can be adapted to or configured to provide for improved binding of the releasable component in some embodiments.

The present disclosure will now be described more fully hereinafter with reference to example embodiments thereof. These example embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in this specification and the claims, the singular forms "a," "an," and "the" include plural referents unless the context clearly dictates otherwise. Reference to "dry weight percent" or "dry weight basis" refers to weight on the basis of dry ingredients (i.e., all ingredients except water). Reference to "wet weight" refers to the weight of the mixture including water. Unless otherwise indicated, reference to "weight percent" of a mixture reflects the total wet weight of the mixture (i.e., including water).

The present disclosure provides compositions and products that can include the compositions. More particularly, the compositions may be provided in a variety of forms and, as further described herein, specifically may be provided in a substantially solid form, such as a collection of particles, fibers, or the like. Accordingly, a product may include the composition itself or the composition positioned within a unitizing structure, such as a pouch or the like. In some embodiments, a composition or product as described herein can comprise a carrier/filler and a releasable material. Preferably, at least a portion of the carrier/filler can be adapted to or configured to include charged groups. Further, in one or more embodiments, at least a portion of the releasable material can be at least partially bound the filler through oppositely charged groups present on the releasable material.

Carrier/Filler Component

Compositions as described herein include at least one component that may be characterized as being a carrier component and/or a filler component. In some embodiments, the compositions may include both of a carrier and a filler, and various materials may fulfill the function of both a carrier and a filler. A carrier component according to the present disclosure preferably may be adapted to or configured to retain at least a releasable material as described herein and may, in some embodiments, retain substantially all of the further components of the composition. A filler component may fulfill multiple functions, such as enhancing certain organoleptic properties such as texture and mouthfeel, enhancing cohesiveness or compressibility of the product, and the like. Generally, the filler components are porous and/or particulate materials. In some embodiments, the present compositions may comprise a carrier. In further embodiments, the present compositions may comprise a carrier and a filler.

In some embodiments, a carrier component and/or a filler component may be cellulose-based. For example, suitable particulate components are any non-tobacco plant material or derivative thereof, including cellulose materials derived from such sources. Examples of cellulosic non-tobacco plant material include cereal grains (e.g., maize, oat, barley, rye, buckwheat, and the like), sugar beet (e.g., FIBREX® brand filler available from International Fiber Corporation), bran fiber, and mixtures thereof. Non-limiting examples of derivatives of non-tobacco plant material include starches (e.g., from potato, wheat, rice, corn), natural cellulose, and modified cellulosic materials. Additional examples of potential particulate carrier and/or filler components include maltodextrin, dextrose, calcium carbonate, calcium phosphate, lactose, mannitol, xylitol, and sorbitol. Combinations of materials can also be used.

"Starch" as used herein may refer to pure starch from any source, modified starch, or starch derivatives. Starch is present, typically in granular form, in almost all green plants and in various types of plant tissues and organs (e.g., seeds, leaves, rhizomes, roots, tubers, shoots, fruits, grains, and stems). Starch can vary in composition, as well as in granular shape and size. Often, starch from different sources has different chemical and physical characteristics. A specific starch can be selected for inclusion in the mixture based on the ability of the starch material to impart a specific organoleptic property to composition. Starches derived from various sources can be used. For example, major sources of starch include cereal grains (e.g., rice, wheat, and maize) and root vegetables (e.g., potatoes and cassava). Other examples of sources of starch include acorns, arrowroot, arracacha, bananas, barley, beans (e.g., favas, lentils, mung beans, peas, chickpeas), breadfruit, buckwheat, canna, chestnuts, colacasia, katakuri, kudzu, malanga, millet, oats, oca, Polynesian arrowroot, sago, sorghum, sweet potato, quinoa, rye, tapioca, taro, tobacco, water chestnuts, and yams. Certain starches are modified starches. A modified starch has undergone one or more structural modifications, often designed to alter its high heat properties. Some starches have been developed by genetic modifications, and are considered to be "modified" starches. Other starches are obtained and subsequently modified. For example, modified starches can be starches that have been subjected to chemical reactions, such as esterification, etherification, oxidation, depolymerization (thinning) by acid catalysis or oxidation in the presence of base, bleaching, transglycosylation and depolymerization (e.g., dextrinization in the presence of a catalyst), cross-linking, enzyme treatment, acetylation, hydroxypropylation, and/or partial hydrolysis. Other starches are modified by heat treatments, such as pregelatinization, dextrinization, and/or cold water swelling processes. Certain modified starches include monostarch phosphate, distarch glycerol, distarch phosphate esterified with sodium trimetaphosphate, phosphate distarch phosphate, acetylated distarch phosphate, starch acetate esterified with acetic anhydride, starch acetate esterified with vinyl acetate, acetylated distarch adipate, acetylated distarch glycerol, hydroxypropyl starch, hydroxypropyl distarch glycerol, starch sodium octenyl succinate.

In some embodiments, a carrier component and/or a filler component may be a cellulose material or cellulose derivative. One particularly suitable material for use in the products described herein is microcrystalline cellulose ("mcc"). The mcc may be synthetic or semi-synthetic, or it may be obtained entirely from natural celluloses. The mcc may be selected from the group consisting of AVICEL® grades PH-100, PH-102, PH-103, PH-105, PH-112, PH-113, PH-200, PH-300, PH-302, VIVACEL® grades 101, 102, 12, 20 and EMOCEL® grades 50M and 90M, and the like, and mixtures thereof. In one embodiment, a composition as described herein may comprise mcc as a particulate filler component and/or as a carrier component. The quantity of mcc present in the compositions as described herein may vary according to the desired properties. In some embodiments, a cellulose derivative or a combination of such derivatives in particular may be used in combination with a different carrier component, and this particularly can include cellulose derivatives, such as a cellulose ether (including carboxyalkyl ethers), meaning a cellulose polymer with the hydrogen of one or more hydroxyl groups in the cellulose structure replaced with an alkyl, hydroxyalkyl, or aryl group. Non-limiting examples of such cellulose derivatives include methylcellulose, hydroxypropylcellulose ("HPC"), hydroxypropylmethylcellulose ("HPMC"), hydroxyethyl cellulose, and carboxymethylcellulose ("CMC"). In one embodiment, the cellulose derivative is one or more of methylcellulose, HPC, HPMC, hydroxyethyl cellulose, and CMC. In one embodiment, the cellulose derivative is HPC.

In some embodiments, a carrier/filler material may comprise one or more charged groups thereon. The charged groups may be inherently present in the material in its substantially normal state. Alternatively, or additionally, the carrier/filler material may be expressly modified to include such group(s). As such, the carrier/filler may be functionalized to include one or more charged functional groups that would not otherwise be expected to present in the substantially normal state of the material. In some embodiments, the charged group(s) may be negatively charged groups. For example, a suitable negatively charged group on a carrier/filler may include one or more carboxyl groups. In other embodiments, one or more phosphate groups, alcohol/hydroxyl groups, and/or halogens may be utilized as the negatively charged group. As a non-limiting example, carboxylated cellulose materials, such as carboxylated microcrystalline cellulose in particular may be used as a carrier/filler material comprising negatively charged groups thereon. In some embodiments, the charged group(s) may be positively charged groups. For example, one or more amine groups may be utilized.

The presence of negatively charged groups on the carrier/filler can be beneficial for stabilizing one or more releasable materials that may be included in the present compositions and products. In particular, any releasable material including one or more positively charged groups thereon may be bound to the carrier/filler through ionic bonding, hydrogen bonding, or similar bonding chemistries so that the releasable material is substantially stabilized in the composition while remaining releasable therefrom when the composition or product is present in an oral cavity.

The total amount of carrier component(s) and filler component(s) present in the composition can vary, but is typically up to about 75 percent of the composition by weight, based on the total weight of the composition. A typical range of total carrier and/or filler component within the composition can be from about 10 to about 75 percent by total weight of the composition, for example, from about 10, about 15, about 20, about 25, or about 30, to about 35, about 40, about 45, or about 50 weight percent (e.g., about 20 to about 50 weight percent or about 25 to about 45 weight percent). In certain embodiments, the total amount of carrier/filler component is at least about 10 percent by weight, such as at least about 20 percent, or at least about 25 percent, or at least about 30 percent, or at least about 35 percent, or at least about 40 percent, based on the total weight of the composition.

In one or more embodiments, a carrier component may be adapted to or configured to substantially surround or envelop further components of the composition. For example, the carrier may be configured as a packet, a pouch, a fleece, or the like, and such structures are further described herein. The term "fleece" may particularly be used herein as a common term for such structures and should not be viewed as limiting the nature of the structure.

A suitable fleece, for example, may be formed of a plurality of fibers. The term "fiber" as used herein includes both fibers of finite length, such as conventional staple fibers and nanofibers, as well as substantially continuous structures, such as continuous filaments, unless otherwise indicated. The fibers can have a substantially round or circular cross section or non-circular cross sections (for example, oval, rectangular, multi-lobed, and the like). The fibers can be provided in a variety of configurations, and the fibers particularly can include multicomponent fibers.

In some embodiments, the fleece can be in the form of a non-woven material. The term "nonwoven" is used herein in reference to fibrous materials, webs, mats, batts, or sheets in which fibers are aligned in an undefined or random orientation. In some embodiments, the plurality of fibers used in forming a fleece may include heat sealable and/or meltable binder fibers. Further aspects of a suitable pouch or fleece are further described below.

Releasable Material

A "releasable material" as used herein may refer to any material that is retained by the filler/carrier that is releasable therefrom when in contact with the oral cavity of a consumer. The releasable material preferably can be adapted to bond with the carrier/filler, such as through ionic bonding, hydrogen bonding, and similar bonding chemistries. In this manner, the releasable material may be retained with a desired level of stability and/or may be configured for release from the carrier/filler. A wide of variety of releasable materials may be utilized. In some embodiments, a plurality of releasable materials may be used. In some embodiments, different releasable materials may be adapted to or configured to preferentially bond with a specific carrier/filler. For example, a first releasable material may include charged groups and thus be adapted to or configured to bond with a carrier/filler including oppositely charged groups, and a second releasable material may be adapted to or configured to be bound with a carrier/filler via other means, such as through being absorbed and/or adsorbed into pores of the carrier/filler.

Active Ingredients

In some embodiments, a releasable material may be an active ingredient. For example, the releasable material may include a single active ingredient or a plurality of active ingredients. If desired, one or more active ingredients may be retained by one or more carrier/filler materials.

Non-limiting examples of active ingredients that may be used as a releasable material herein and/or be otherwise included within the present compositions and/or products can include a nicotine component, botanical ingredients (e.g., hemp, lavender, peppermint, *Eucalyptus*, rooibos, fennel, cloves, chamomile, basil, rosemary, clove, citrus, ginger, *Cannabis*, *Ginseng*, maca, and tisanes), stimulants (e.g., caffeine and guarana), amino acids (e.g., taurine, theanine, phenylalanine, tyrosine, and tryptophan), and/or pharmaceutical, nutraceutical, and medicinal ingredients (e.g., vitamins, such as B6, B12, and C, and/or cannabinoids, such as tetrahydrocannabinol (THC) and cannabidiol (CBD)). The particular percentages and choice of ingredients can vary depending upon the desired flavor, texture, and other characteristics. Example active ingredients would include any ingredient known to impact one or more biological functions within the body, such as ingredients that furnish pharmacological activity or other direct effect in the diagnosis, cure, mitigation, treatment, or prevention of disease, or which affect the structure or any function of the body of humans or other animals (e.g., provide a stimulating action on the central nervous system, have an energizing effect, an antipyretic or analgesic action, or an otherwise useful effect on the body).

In some embodiments, an active ingredient may comprise one or more charged groups thereon. The charged groups may be inherently present in the active ingredient in its substantially normal state. Alternatively, or additionally, the active ingredient may be expressly modified to include such group(s). As such, the active ingredient may be functionalized to include one or more charged functional groups that would not otherwise be expected to present in the substantially normal state of the material. In some embodiments, the charged group(s) may be positively charged groups. In other embodiments, the charged group(s) may be negatively charged groups. The charged groups on the active ingredient can be such that the active ingredient will be adapted to or configured to be retained by the carrier/filler material as discussed above through bonding of the charged groups on the active ingredient with the oppositely charged groups on the carrier/filler. Preferably, the engagement/bonding/retaining between the active ingredient and the carrier/filler is such that at least a portion of the active ingredient is adapted to or configured to be released from the composition or product when the composition or product is present in the oral cavity of a consumer.

In certain embodiments, a nicotine component may be included in the mixture. By "nicotine component" is meant any suitable form of nicotine (e.g., free base or salt) for providing oral absorption of at least a portion of the nicotine present. Typically, the nicotine component is selected from the group consisting of nicotine free base and a nicotine salt. In some embodiments, nicotine is in its free base form, which easily can be adsorbed in for example, a microcrystalline cellulose material to form a microcrystalline cellulose-nicotine carrier complex. See, for example, the discussion of nicotine in free base form in US Pat. Pub. No. 2004/0191322 to Hansson, which is incorporated herein by reference.

In some embodiments, at least a portion of the nicotine can be employed in the form of a salt. Salts of nicotine can be provided using the types of ingredients and techniques set forth in U.S. Pat. No. 2,033,909 to Cox et al. and Perfetti, *Beitrage Tabakforschung Int.*, 12: 43-54 (1983), which are incorporated herein by reference. Additionally, salts of nicotine are available from sources such as Pfaltz and Bauer, Inc. and K&K Laboratories, Division of ICN Biochemicals, Inc.

Typically, the nicotine component is selected from the group consisting of nicotine free base, a nicotine salt such as hydrochloride, dihydrochloride, monotartrate, bitartrate, sulfate, salicylate, and nicotine zinc chloride. In some embodiments, the nicotine component or a portion thereof is a nicotine salt. A nicotine salt is a form of nicotine characterized by the interaction between nicotine in ionic form and a co-former in ionic form (e.g., an acid) via the transfer of one or more protons from the co-former donor to the nicotine acceptor. The structure of nicotine is such that it comprises two nitrogen atoms that are capable of accepting protons from a co-former and, accordingly, it can be present in non-protonated, mono-protonated, and/or di-protonated form in a given sample. Protonated nicotine therefore is a non-limiting example of a positively charged active ingredient that may be combined with a carrier/filler including negatively charged groups thereon. More particularly, protonated nicotine may include an amine group that may be positively charged as noted above. Likewise, other active ingredients may include amine groups or similar, positively charged groups and thus may be used according to the present disclosure.

In some embodiments, at least a portion of the nicotine can be in the form of a resin complex of nicotine, where nicotine is bound in an ion-exchange resin, such as nicotine polacrilex, which is nicotine bound to, for example, a polymethacrilic acid, such as Amberlite IRP64, Purolite C115HMR, or Doshion P551. See, for example, U.S. Pat. No. 3,901,248 to Lichtneckert et al., which is incorporated herein by reference. Another example is a nicotine-polyacrylic carbomer complex, such as with Carbopol 974P. In some embodiments, nicotine may be present in the form of a nicotine polyacrylic complex.

Typically, the nicotine component (calculated as the free base or as the protonated form) when present, is in a concentration of at least about 0.001% by weight of the mixture, such as in a range from about 0.001% to about 10%. In some embodiments, the nicotine component is present in a concentration from about 0.1% w/w to about 10% by weight, such as, e.g., from about from about 0.1% w/w, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, or about 10% by weight, calculated as the free base and based on the total weight of the mixture. In some embodiments, the nicotine component is present in a concentration from about 0.1% w/w to about 3% by weight, such as, e.g., from about from about 0.1% w/w to about 2.5%, from about 0.1% to about 2.0%, from about 0.1% to about 1.5%, or from about 0.1% to about 1% by weight, calculated as the free base and based on the total weight of the mixture. These ranges can also apply to other active ingredients noted herein.

In one or more embodiments, nicotine in particular may be utilized as a charged group to be carried via interactions as described herein. Other non-limiting examples of suitable active ingredients that may be utilized in such manner include, but are not limited to, caffeine, theobromine, eugenol, geraniol, flavonoids, polyphenols, and the like.

Flavoring Agents

In some embodiments, a releasable material may be a flavoring agent. As used herein, a "flavoring agent" or "flavorant" is any flavorful or aromatic substance capable of altering the sensory characteristics associated with the oral product. Examples of sensory characteristics that can be modified by the flavoring agent include taste, mouthfeel, moistness, coolness/heat, and/or fragrance/aroma. Flavoring agents may be natural or synthetic, and the character of the flavors imparted thereby may be described, without limitation, as fresh, sweet, herbal, confectionary, floral, fruity, or spicy. In some embodiments, the releasable material may include a single flavoring agent or a plurality of flavoring agents. If desired, one or more flavoring agents may be retained by one or more carrier/filler materials as described herein.

Non-limiting examples of flavoring agents that may be used as a releasable material herein and/or be otherwise included within the present compositions and/or products can include vanilla, coffee, chocolate/cocoa, cream, mint, spearmint, menthol, peppermint, wintergreen, *Eucalyptus*, lavender, cardamom, nutmeg, cinnamon, clove, *Cascarilla*, sandalwood, honey, jasmine, ginger, anise, sage, licorice, lemon, orange, apple, peach, lime, cherry, strawberry, trigeminal sensates, terpenes, and any combinations thereof. See also, Leffingwell et al., Tobacco Flavoring for Smoking Products, R. J. Reynolds Tobacco Company (1972), which is incorporated herein by reference. Flavoring agents may comprise components such as terpenes, terpenoids, aldehydes, ketones, esters, and the like. In some embodiments, the flavoring agent is a trigeminal sensate. As used herein, "trigeminal sensate" refers to a flavoring agent which has an effect on the trigeminal nerve, producing sensations including heating, cooling, tingling, and the like. Non-limiting examples of trigeminal sensate flavoring agents include capsaicin, citric acid, menthol, Sichuan buttons, erythritol, and cubebol. Flavorings also may include components that are considered moistening, cooling or smoothening agents, such as *Eucalyptus*. These flavors may be provided neat (i.e., alone) or in a composite, and may be employed as concentrates or flavor packages (e.g., spearmint and menthol, orange and cinnamon; lime, pineapple, and the like). Representative types of components also are set forth in U.S. Pat. No. 5,387,416 to White et al.; US Pat. App. Pub. No. 2005/0244521 to Strickland et al.; and PCT Application Pub. No. WO 05/041699 to Quinter et al., each of which is incorporated herein by reference. In some instances, the flavoring agent may be provided in a spray-dried form or a liquid form.

The flavoring agent generally comprises at least one volatile flavor component. As used herein, "volatile" refers to a chemical substance that forms a vapor readily at ambient temperatures (i.e., a chemical substance that has a high vapor pressure at a given temperature relative to a nonvolatile substance). Typically, a volatile flavor component has a molecular weight below about 400 Da, and often include at least one carbon-carbon double bond, carbon-oxygen double bond, or both. In one embodiment, the at least one volatile flavor component comprises one or more alcohols, aldehydes, aromatic hydrocarbons, ketones, esters, terpenes, terpenoids, or a combination thereof. Non-limiting examples of aldehydes include vanillin, ethyl vanillin, p-anisaldehyde, hexanal, furfural, isovaleraldehyde, cuminaldehyde, benzaldehyde, and citronellal. Non-limiting examples of ketones include 1-hydroxy-2-propanone and 2-hydroxy-3-methyl-2-cyclopentenone-1-one. Non-limiting examples of esters include allyl hexanoate, ethyl heptanoate, ethyl hexanoate, isoamyl acetate, and 3-methylbutyl acetate. Non-limiting examples of terpenes include sabinene, limonene, gamma-terpinene, beta-farnesene, nerolidol, thujone, myrcene, geraniol, nerol, citronellol, linalool, and eucalyptol. In one embodiment, the at least one volatile flavor component comprises one or more of ethyl vanillin, cinnamaldehyde, sabinene, limonene, gamma-terpinene, beta-farnesene, or citral. In one embodiment, the at least one volatile flavor component comprises ethyl vanillin.

The amount of flavoring agent utilized in the mixture can vary, but is typically up to about 10 weight percent, and certain embodiments are characterized by a flavoring agent content of at least about 0.1 weight percent, such as about 0.5 to about 10 weight percent, about 1 to about 6 weight percent, or about 2 to about 5 weight percent, based on the total weight of the mixture.

Tobacco Material

In some embodiments, the present compositions and/or products may include a tobacco material. The tobacco material can vary in species, type, and form. Generally, the tobacco material is obtained from for a harvested plant of the *Nicotiana* species. Example *Nicotiana* species include *N. tabacum, N. rustica, N. alata, N. arentsii, N. excelsior, N. forgetiana, N. glauca, N. glutinosa, N. gossei, N. kawakamii, N. knightiana, N. langsdorffi, N. otophora, N. setchelli, N. sylvestris, N. tomentosa, N. tomentosiformis, N. undulata,* N. x *sanderae, N. africana, N. amplexicaulis, N. benavidesii, N. bonariensis, N. debneyi, N. longiflora, N. maritina, N. megalosiphon, N. occidentalis, N. paniculata, N. plumbaginifolia, N. raimondii, N. rosulata, N. simulans, N. stocktonii, N. suaveolens, N. umbratica, N. velutina, N. wigandioides, N. acaulis, N. acuminata, N. attenuata, N. benthamiana, N. cavicola, N. clevelandii, N. cordifolia, N. corymbosa, N. fragrans, N. goodspeedii, N. linearis, N. miersii, N. nudicaulis, N. obtusifolia, N. occidentalis* subsp. *Hersperis, N. pauciflora, N. petunioides, N. quadrivalvis, N. repanda, N. rotundifolia, N. solanifolia,* and *N. spegazzinii*. Various representative other types of plants from the *Nicotiana* species are set forth in Goodspeed, The Genus *Nicotiana*, (Chonica Botanica) (1954); U.S. Pat. No. 4,660,577 to Sensabaugh, Jr. et al.; U.S. Pat. No. 5,387,416 to White et al., U.S. Pat. No. 7,025,066 to Lawson et al.; U.S. Pat. No. 7,798,153 to Lawrence, Jr. and U.S. Pat. No. 8,186,360 to Marshall et al.; each of which is incorporated herein by reference. Descriptions of various types of tobaccos, growing practices and harvesting practices are set forth in *Tobacco Production, Chemistry and Technology*, Davis et al. (Eds.) (1999), which is incorporated herein by reference.

*Nicotiana* species from which suitable tobacco materials can be obtained can be derived using genetic-modification or crossbreeding techniques (e.g., tobacco plants can be genetically engineered or crossbred to increase or decrease production of components, characteristics or attributes). See, for example, the types of genetic modifications of plants set forth in U.S. Pat. No. 5,539,093 to Fitzmaurice et al.; U.S. Pat. No. 5,668,295 to Wahab et al.; U.S. Pat. No. 5,705,624 to Fitzmaurice et al.; U.S. Pat. No. 5,844,119 to Weigl; U.S. Pat. No. 6,730,832 to Dominguez et al.; U.S. Pat. No. 7,173,170 to Liu et al.; U.S. Pat. No. 7,208,659 to Colliver et al. and U.S. Pat. No. 7,230,160 to Benning et al.; US Patent Appl. Pub. No. 2006/0236434 to Conkling et al.; and PCT WO2008/103935 to Nielsen et al. See, also, the types of tobaccos that are set forth in U.S. Pat. No. 4,660,577 to Sensabaugh, Jr. et al.; U.S. Pat. No. 5,387,416 to White et al.; and U.S. Pat. No. 6,730,832 to Dominguez et al., each of which is incorporated herein by reference.

The *Nicotiana* species can, in some embodiments, be selected for the content of various compounds that are present therein. For example, plants can be selected on the basis that those plants produce relatively high quantities of one or more of the compounds desired to be isolated therefrom. In certain embodiments, plants of the *Nicotiana* species (e.g., *Galpao commun* tobacco) are specifically grown for their abundance of leaf surface compounds. Tobacco plants can be grown in greenhouses, growth chambers, or outdoors in fields, or grown hydroponically.

Various parts or portions of the plant of the *Nicotiana* species can be included within a mixture as disclosed herein. For example, virtually all of the plant (e.g., the whole plant) can be harvested, and employed as such. Alternatively, various parts or pieces of the plant can be harvested or separated for further use after harvest. For example, the flower, leaves, stem, stalk, roots, seeds, and various combinations thereof, can be isolated for further use or treatment. In some embodiments, the tobacco material comprises tobacco leaf (lamina). The mixture disclosed herein can include processed tobacco parts or pieces, cured and aged tobacco in essentially natural lamina and/or stem form, a tobacco extract, extracted tobacco pulp (e.g., using water as a solvent), or a mixture of the foregoing (e.g., a mixture that combines extracted tobacco pulp with granulated cured and aged natural tobacco lamina).

In certain embodiments, the tobacco material comprises solid tobacco material selected from the group consisting of lamina and stems. The tobacco that is used for the mixture most preferably includes tobacco lamina, or a tobacco lamina and stem mixture (of which at least a portion is smoke-treated). Portions of the tobaccos within the mixture may have processed forms, such as processed tobacco stems (e.g., cut-rolled stems, cut-rolled-expanded stems or cut-puffed stems), or volume expanded tobacco (e.g., puffed tobacco, such as dry ice expanded tobacco (DIET)). See, for example, the tobacco expansion processes set forth in U.S. Pat. No. 4,340,073 to de la Burde et al.; U.S. Pat. No. 5,259,403 to Guy et al.; and U.S. Pat. No. 5,908,032 to Poindexter, et al.; and U.S. Pat. No. 7,556,047 to Poindexter, et al., all of which are incorporated by reference. In addition, the d mixture optionally may incorporate tobacco that has been fermented. See, also, the types of tobacco processing techniques set forth in PCT WO2005/063060 to Atchley et al., which is incorporated herein by reference.

The tobacco material is typically used in a form that can be described as particulate (i.e., shredded, ground, granulated, or powder form). The manner by which the tobacco material is provided in a finely divided or powder type of form may vary. Preferably, plant parts or pieces are comminuted, ground or pulverized into a particulate form using equipment and techniques for grinding, milling, or the like. Most preferably, the plant material is relatively dry in form during grinding or milling, using equipment such as hammer mills, cutter heads, air control mills, or the like. For example, tobacco parts or pieces may be ground or milled when the moisture content thereof is less than about 15 weight percent or less than about 5 weight percent. Most preferably, the tobacco material is employed in the form of parts or pieces that have an average particle size between 1.4 millimeters and 250 microns. In some instances, the tobacco particles may be sized to pass through a screen mesh to obtain the particle size range required. If desired, air classification equipment may be used to ensure that small sized tobacco particles of the desired sizes, or range of sizes, may be collected. If desired, differently sized pieces of granulated tobacco may be mixed together.

The manner by which the tobacco is provided in a finely divided or powder type of form may vary. Preferably, tobacco parts or pieces are comminuted, ground or pulverized into a powder type of form using equipment and techniques for grinding, milling, or the like. Most preferably, the tobacco is relatively dry in form during grinding or milling, using equipment such as hammer mills, cutter heads, air control mills, or the like. For example, tobacco parts or pieces may be ground or milled when the moisture content thereof is less than about 15 weight percent to less than about 5 weight percent. For example, the tobacco plant or portion thereof can be separated into individual parts or pieces (e.g., the leaves can be removed from the stems, and/or the stems and leaves can be removed from the stalk). The harvested plant or individual parts or pieces can be further subdivided into parts or pieces (e.g., the leaves can be shredded, cut, comminuted, pulverized, milled or ground into pieces or parts that can be characterized as filler-type pieces, granules, particulates or fine powders). The plant, or parts thereof, can be subjected to external forces or pressure (e.g., by being pressed or subjected to roll treatment). When carrying out such processing conditions, the plant or portion thereof can have a moisture content that approximates its natural moisture content (e.g., its moisture content immediately upon harvest), a moisture content achieved by adding moisture to the plant or portion thereof, or a moisture content that results from the drying of the plant or portion thereof. For example, powdered, pulverized, ground or milled pieces of plants or portions thereof can have moisture contents of less than about 25 weight percent, often less than about 20 weight percent, and frequently less than about 15 weight percent.

For the preparation of oral products, it is typical for a harvested plant of the *Nicotiana* species to be subjected to a curing process. The tobacco materials incorporated within the mixture for inclusion within products as disclosed herein are those that have been appropriately cured and/or aged. Descriptions of various types of curing processes for various types of tobaccos are set forth in *Tobacco Production, Chemistry and Technology*, Davis et al. (Eds.) (1999). Examples of techniques and conditions for curing flue-cured tobacco are set forth in Nestor et al., *Beitrage Tabakforsch. Int.*, 20, 467-475 (2003) and U.S. Pat. No. 6,895,974 to Peele, which are incorporated herein by reference. Representative techniques and conditions for air curing tobacco are set forth in U.S. Pat. No. 7,650,892 to Groves et al.; Roton et al., *Beitrage Tabakforsch. Int.*, 21, 305-320 (2005) and Staaf et al., *Beitrage Tabakforsch. Int.*, 21, 321-330 (2005), which are incorporated herein by reference. Certain types of tobaccos can be subjected to alternative types of curing processes, such as fire curing or sun curing.

In certain embodiments, tobacco materials that can be employed include flue-cured or Virginia (e.g., K326), burley, sun-cured (e.g., Indian Kurnool and Oriental tobaccos, including Katerini, Prelip, Komotini, Xanthi and Yambol tobaccos), Maryland, dark, dark-fired, dark air cured (e.g., Madole, Passanda, Cubano, Jatin and Bezuki tobaccos), light air cured (e.g., North Wisconsin and *Galpao* tobaccos), Indian air cured, Red Russian and *Rustica* tobaccos, as well as various other rare or specialty tobaccos and various blends of any of the foregoing tobaccos.

The tobacco material may also have a so-called "blended" form. For example, the tobacco material may include a mixture of parts or pieces of flue-cured, burley (e.g., Malawi burley tobacco) and Oriental tobaccos (e.g., as tobacco composed of, or derived from, tobacco lamina, or a mixture of tobacco lamina and tobacco stem). For example, a representative blend may incorporate about 30 to about 70 parts burley tobacco (e.g., lamina, or lamina and stem), and about 30 to about 70 parts flue cured tobacco (e.g., stem, lamina, or lamina and stem) on a dry weight basis. Other example tobacco blends incorporate about 75 parts flue-cured tobacco, about 15 parts burley tobacco, and about 10 parts Oriental tobacco; or about 65 parts flue-cured tobacco, about 25 parts burley tobacco, and about 10 parts Oriental tobacco; or about 65 parts flue-cured tobacco, about 10 parts burley tobacco, and about 25 parts Oriental tobacco; on a dry weight basis. Other example tobacco blends incorporate about 20 to about 30 parts Oriental tobacco and about 70 to about 80 parts flue-cured tobacco on a dry weight basis.

Tobacco materials used in the present disclosure can be subjected to, for example, fermentation, bleaching, and the like. If desired, the tobacco materials can be, for example, irradiated, pasteurized, or otherwise subjected to controlled heat treatment. Such treatment processes are detailed, for example, in U.S. Pat. No. 8,061,362 to Mua et al., which is incorporated herein by reference. In certain embodiments, tobacco materials can be treated with water and an additive capable of inhibiting reaction of asparagine to form acrylamide upon heating of the tobacco material (e.g., an additive selected from the group consisting of lysine, glycine, histidine, alanine, methionine, cysteine, glutamic acid, aspartic acid, proline, phenylalanine, valine, arginine, compositions incorporating di- and trivalent cations, asparaginase, certain non-reducing saccharides, certain reducing agents, phenolic compounds, certain compounds having at least one free thiol group or functionality, oxidizing agents, oxidation catalysts, natural plant extracts (e.g., rosemary extract), and combinations thereof. See, for example, the types of treatment processes described in U.S. Pat. Nos. 8,434,496, 8,944,072, and 8,991,403 to Chen et al., which are all incorporated herein by reference. In certain embodiments, this type of treatment is useful where the original tobacco material is subjected to heat in the processes previously described.

In some embodiments, the type of tobacco material is selected such that it is initially visually lighter in color than other tobacco materials to some degree (e.g., whitened or bleached). Tobacco pulp can be whitened in certain embodiments according to any means known in the art. For example, bleached tobacco material produced by various whitening methods using various bleaching or oxidizing agents and oxidation catalysts can be used. Example oxidizing agents include peroxides (e.g., hydrogen peroxide), chlorite salts, chlorate salts, perchlorate salts, hypochlorite salts, ozone, ammonia, potassium permanganate, and combinations thereof. Example oxidation catalysts are titanium dioxide, manganese dioxide, and combinations thereof. Processes for treating tobacco with bleaching agents are discussed, for example, in US Patent No. 787,611 to Daniels, Jr.; U.S. Pat. No. 1,086,306 to Oelenheinz; U.S. Pat. No. 1,437,095 to Delling; U.S. Pat. No. 1,757,477 to Rosenhoch; U.S. Pat. No. 2,122,421 to Hawkinson; U.S. Pat. No. 2,148,147 to Baier; U.S. Pat. No. 2,170,107 to Baier; U.S. Pat. No. 2,274,649 to Baier; U.S. Pat. No. 2,770,239 to Prats et al.; U.S. Pat. No. 3,612,065 to Rosen; U.S. Pat. No. 3,851,653 to Rosen; U.S. Pat. No. 3,889,689 to Rosen; U.S. Pat. No. 3,943,940 to Minami; U.S. Pat. No. 3,943,945 to Rosen; U.S. Pat. No. 4,143,666 to Rainer; U.S. Pat. No. 4,194,514 to Campbell; U.S. Pat. Nos. 4,366,823, 4,366,824, and 4,388,933 to Rainer et al.; U.S. Pat. No. 4,641,667 to Schmekel et al.; U.S. Pat. No. 5,713,376 to Berger; U.S. Pat. No. 9,339,058 to Byrd Jr. et al.; U.S. Pat. No. 9,420,825 to Beeson et al.; and U.S. Pat. No. 9,950,858 to Byrd Jr. et al.; as well as in US Pat. App. Pub. Nos. 2012/0067361 to Bjorkholm et al.; 2016/0073686 to Crooks; 2017/0020183 to Bjorkholm; and 2017/0112183 to Bjorkholm, and in PCT Publ. Appl. Nos. WO1996/031255 to Giolvas and WO2018/083114 to Bjorkholm, all of which are incorporated herein by reference.

In some embodiments, the whitened tobacco material can have an ISO brightness of at least about 50%, at least about 60%, at least about 65%, at least about 70%, at least about 75%, or at least about 80%. In some embodiments, the whitened tobacco material can have an ISO brightness in the range of about 50% to about 90%, about 55% to about 75%, or about 60% to about 70%. ISO brightness can be measured according to ISO 3688:1999 or ISO 2470-1:2016.

In some embodiments, the whitened tobacco material can be characterized as lightened in color (e.g., "whitened") in comparison to an untreated tobacco material. White colors are often defined with reference to the International Commission on Illumination's (CIE's) chromaticity diagram. The whitened tobacco material can, in certain embodiments, be characterized as closer on the chromaticity diagram to pure white than an untreated tobacco material.

In various embodiments, the tobacco material can be treated to extract a soluble component of the tobacco material therefrom. "Tobacco extract" as used herein refers to the isolated components of a tobacco material that are extracted from solid tobacco pulp by a solvent that is brought into contact with the tobacco material in an extraction process. Various extraction techniques of tobacco materials can be used to provide a tobacco extract and tobacco solid material. See, for example, the extraction processes described in US Pat. Appl. Pub. No. 2011/0247640 to Beeson et al., which is incorporated herein by reference. Other example techniques for extracting components of tobacco are described in U.S. Pat. No. 4,144,895 to Fiore; U.S. Pat. No. 4,150,677 to Osborne, Jr. et al.; U.S. Pat. No. 4,267,847 to Reid; U.S. Pat. No. 4,289,147 to Wildman et al.; U.S. Pat. No. 4,351,346 to Brummer et al.; U.S. Pat. No. 4,359,059 to Brummer et al.; U.S. Pat. No. 4,506,682 to Muller; U.S. Pat. No. 4,589,428 to Keritsis; U.S. Pat. No. 4,605,016 to Soga et al.; U.S. Pat. No. 4,716,911 to Poulose et al.; U.S. Pat. No. 4,727,889 to Niven, Jr. et al.; U.S. Pat. No. 4,887,618 to Bernasek et al.; U.S. Pat. No. 4,941,484 to Clapp et al.; U.S. Pat. No. 4,967,771 to Fagg et al.; U.S. Pat. No. 4,986,286 to Roberts et al.; U.S. Pat. No. 5,005,593 to Fagg et al.; U.S. Pat. No. 5,018,540 to Grubbs et al.; U.S. Pat. No. 5,060,669 to White et al.; U.S. Pat. No. 5,065,775 to Fagg; U.S. Pat. No. 5,074,319 to White et al.; U.S. Pat. No. 5,099,862 to White et al.; U.S. Pat. No. 5,121,757 to White et al.; U.S. Pat. No. 5,131,414 to Fagg; U.S. Pat. No. 5,131,415 to Munoz et al.; U.S. Pat. No. 5,148,819 to Fagg; U.S. Pat. No. 5,197,494 to Kramer; U.S. Pat. No. 5,230,354 to Smith et al.; U.S. Pat. No. 5,234,008 to Fagg; U.S. Pat. No. 5,243,999 to Smith; U.S. Pat. No. 5,301,694 to Raymond et al.; U.S. Pat. No. 5,318,050 to Gonzalez-Parra et al.; U.S. Pat. No. 5,343,879 to Teague; U.S. Pat. No. 5,360,022 to Newton; U.S. Pat. No. 5,435,325 to Clapp et al.; U.S. Pat. No. 5,445,169 to Brinkley et al.; U.S. Pat. No. 6,131,584 to Lauterbach; U.S. Pat. No. 6,298,859 to Kierulff et al.; U.S. Pat. No. 6,772,767 to Mua et al.; and U.S. Pat. No. 7,337,782 to Thompson, all of which are incorporated by reference herein.

Typical inclusion ranges for tobacco materials can vary depending on the nature and type of the tobacco material, and the intended effect on the final mixture, with an example range of up to about 30% by weight (or up to about 20% by weight or up to about 10% by weight or up to about 5% by weight), based on total weight of the mixture (e.g., about 0.1 to about 15% by weight). In some embodiments, the products of the disclosure can be characterized as completely free or substantially free of tobacco material (other than purified nicotine as an active ingredient). For example, certain embodiments can be characterized as having less than 1% by weight, or less than 0.5% by weight, or less than 0.1% by weight of tobacco material, or 0% by weight of tobacco material. In some embodiments, a composition or product according to the present disclosure may comprise no more than about 10% by weight of a tobacco material, excluding any nicotine component present, based on the total weight of the mixture.

Further Additives

In some embodiments, one or more further additives can be included in the disclosed compositions and/or products. For example, the compositions can be processed, blended, formulated, combined and/or mixed with other materials or ingredients. The additives can be artificial, or can be obtained or derived from herbal or biological sources. Specific types of further additives that may be included are further described below.

In some embodiments, the compositions and products may include a content of water. The water content of the composition within the product, prior to use by a consumer of the product, may vary according to the desired properties. Typically, the composition, as present within the product prior to insertion into the mouth of the user, can comprise less than 60%, less than 50%, less than 40%, less than 30%, less than 20%, less than 10%, or less than 5% by weight of water. For example, total water content in the composition and/or product may be in the range of about 0.1% to about 60%, about 1% to about 50%, about 1.5% to about 40%, or about 2% to about 25% by weight of water. In some embodiments, the compositions and products may include at least 1%, at least 2%, at least 5%, at least 10%, or at least 20% by weight water.

In some embodiments, the compositions and products may include a content of one or more organic acids. As used herein, the term "organic acid" refers to an organic (i.e., carbon-based) compound that is characterized by acidic properties. Typically, organic acids are relatively weak acids (i.e., they do not dissociate completely in the presence of water), such as carboxylic acids ($—CO_2H$) or sulfonic acids ($—SO_2OH$). As used herein, reference to organic acid means an organic acid that is intentionally added. In this regard, an organic acid may be intentionally added as a specific ingredient as opposed to merely being inherently present as a component of another ingredient (e.g., the small amount of organic acid which may inherently be present in an ingredient such as a tobacco material). In some embodiments, the one or more organic acids are added neat (i.e., in their free acid, native solid or liquid form) or as a solution in, e.g., water. In some embodiments, the one or more organic acids are added in the form of a salt, as described herein below.

In some embodiments, the organic acid is an alkyl carboxylic acid. Non-limiting examples of alkyl carboxylic acids include formic acid, acetic acid, propionic acid, octanoic acid, nonanoic acid, decanoic acid, undecanoic acid, dodecanoic acid, stearic acid, oleic acid, linoleic acid, linolenic acid, and the like. In some embodiments, the organic acid is an alkyl sulfonic acid. Non-limiting examples of alkyl sulfonic acids include propanesulfonic acid and octanesulfonic acid. In some embodiments, the alkyl carboxylic or sulfonic acid is substituted with one or more hydroxyl groups. Non-limiting examples include glycolic acid, 4-hydroxybutyric acid, and lactic acid. In some embodiments, an organic acid may include more than one carboxylic acid group or more than one sulfonic acid group (e.g., two, three, or more carboxylic acid groups). Non-limiting examples include oxalic acid, fumaric acid, maleic acid, and glutaric acid. In organic acids containing multiple carboxylic acids (e.g., from two to four carboxylic acid groups), one or more of the carboxylic acid groups may be esterified. Non-limiting examples include succinic acid monoethyl ester, monomethyl fumarate, monomethyl or dimethyl citrate, and the like.

In some embodiments, the organic acid may include more than one carboxylic acid group and one or more hydroxyl groups. Non-limiting examples of such acids include tartaric acid, citric acid, and the like. In some embodiments, the organic acid is an aryl carboxylic acid or an aryl sulfonic acid. Non-limiting examples of aryl carboxylic and sulfonic acids include benzoic acid, toluic acids, salicylic acid, benzenesulfonic acid, and p-toluenesulfonic acid. In some embodiments, the organic acid is citric acid, malic acid, tartaric acid, octanoic acid, benzoic acid, a toluic acid, salicylic acid, or a combination thereof. In some embodiments, the organic acid is benzoic acid. In some embodiments, the organic acid is citric acid. In alternative embodiments, a portion, or even all, of the organic acid may be added in the form of a salt with an alkaline component, which may include, but is not limited to, nicotine. Non-limiting examples of suitable salts, e.g., for nicotine, include formate, acetate, propionate, isobutyrate, butyrate, alpha-methylbutyate, isovalerate, beta-methylvalerate, caproate, 2-furoate, phenylacetate, heptanoate, octanoate, nonanoate, oxalate, malonate, glycolate, benzoate, tartrate, levulinate, ascorbate, fumarate, citrate, malate, lactate, aspartate, salicylate, tosylate, succinate, pyruvate, and the like.

The amount of organic acid present in the compositions may vary. Generally, the compositions can comprise from 0 to about 10% by weight of organic acid, present as one or more organic acids, based on the total weight of the mixture.

In some embodiments, the compositions may further comprise a salt (e.g., alkali metal salts), typically employed in an amount sufficient to provide desired sensory attributes to the compositions and products. Non-limiting examples of suitable salts include sodium chloride, potassium chloride, ammonium chloride, flour salt, and the like. When present, a representative amount of salt is about 0.5 percent by weight or more, about 1.0 percent by weight or more, or at about 1.5 percent by weight or more, but will typically make up about 10 percent or less of the total weight of the composition or product, or about 7.5 percent or less or about 5 percent or less (e.g., about 0.5 to about 5 percent by weight).

The compositions and products also may include one or more sweeteners. The sweeteners can be any sweetener or combination of sweeteners, in natural or artificial form, or as a combination of natural and artificial sweeteners. Examples of natural sweeteners include fructose, sucrose, glucose, maltose, mannose, galactose, lactose, *Stevia*, honey, and the like. Examples of artificial sweeteners include sucralose, isomaltulose, maltodextrin, saccharin, aspartame, acesulfame K, neotame and the like. In some embodiments, the sweetener comprises one or more sugar alcohols. Sugar alcohols are polyols derived from monosaccharides or disaccharides that have a partially or fully hydrogenated form. Sugar alcohols have, for example, about 4 to about 20 carbon atoms and include erythritol, arabitol, ribitol, isomalt, maltitol, dulcitol, iditol, mannitol, xylitol, lactitol, sorbitol, and combinations thereof (e.g., hydrogenated starch hydrolysates). When present, a representative amount of sweetener may make up from about 0.1 to about 20 percent or more of the of the composition by weight, for example, from about 0.1 to about 1%, from about 1 to about 5%, from about 5 to about 10%, or from about 10 to about 20% of the composition or product on a weight basis, based on the total weight of the composition or product.

In some embodiments, the compositions and products may include one or more binding agents. A binder (or combination of binders) may be employed in certain embodiments, in amounts sufficient to provide the desired physical attributes and physical integrity to the composition. Typical binders can be organic or inorganic, or a combination thereof. Representative binders include povidone, sodium alginate, starch-based binders, pectin, carrageenan, pullulan, zein, and the like, and combinations thereof. A binder may be employed in amounts sufficient to provide the desired physical attributes and physical integrity to the composition. The amount of binder utilized can vary, but is typically up to about 30 weight percent, and certain embodiments are characterized by a binder content of at least about 0.1% by weight, such as about 1 to about 30% by weight, or about 5 to about 10% by weight, based on the total weight of the composition or product.

In certain embodiments, the binder includes a gum, for example, a natural gum. As used herein, a natural gum refers to polysaccharide materials of natural origin that have binding properties, and which are also useful as a thickening or gelling agents. Representative natural gums derived from plants, which are typically water soluble to some degree, include xanthan gum, guar gum, gum arabic, ghatti gum, gum tragacanth, karaya gum, locust bean gum, gellan gum, and combinations thereof. When present, natural gum binder materials are typically present in an amount of up to about 5% by weight, for example, from about 0.1, about 0.2, about 0.3, about 0.4, about 0.5, about 0.6, about 0.7, about 0.8, about 0.9, or about 1%, to about 2, about 3, about 4, or about 5% by weight, based on the total weight of the composition or product.

In certain embodiments, one or more humectants may be employed in the compositions. Examples of humectants include, but are not limited to, glycerin, propylene glycol, and the like. Where included, the humectant is typically provided in an amount sufficient to provide desired moisture attributes to the compositions. Further, in some instances, the humectant may impart desirable flow characteristics to the composition for depositing in a mold. When present, a humectant will typically make up about 5% or less of the weight of the composition or product (e.g., from about 0.5 to about 5% by weight). When present, a representative amount of humectant is about 0.1% to about 1% by weight, or about 1% to about 5% by weight, based on the total weight of the composition or product.

In certain embodiments, the compositions of the present disclosure can comprise pH adjusters or buffering agents. Examples of pH adjusters and buffering agents that can be used include, but are not limited to, metal hydroxides (e.g., alkali metal hydroxides such as sodium hydroxide and potassium hydroxide), and other alkali metal buffers such as metal carbonates (e.g., potassium carbonate or sodium carbonate), or metal bicarbonates such as sodium bicarbonate, and the like. Where present, the buffering agent is typically present in an amount less than about 5 percent based on the weight of the compositions or products, for example, from about 0.5% to about 5%, such as, e.g., from about 0.75% to about 4%, from about 0.75% to about 3%, or from about 1% to about 2% by weight, based on the total weight of the compositions or products. Non-limiting examples of suitable buffers include alkali metals acetates, glycinates, phosphates, glycerophosphates, citrates, carbonates, hydrogen carbonates, borates, or mixtures thereof.

In some embodiments, the compositions and products may include one or more colorants. A colorant may be employed in amounts sufficient to provide the desired physical attributes to the composition or product. Examples of colorants include various dyes and pigments, such as caramel coloring and titanium dioxide. The amount of colorant utilized in the compositions or products can vary, but when present is typically up to about 3 weight percent, such as from about 0.1%, about 0.5%, or about 1%, to about 3% by weight, based on the total weight of the composition or product.

Examples of even further types of additives that may be used in the present compositions and products include thickening or gelling agents (e.g., fish gelatin), emulsifiers, oral care additives (e.g., thyme oil, *Eucalyptus* oil, and zinc), preservatives (e.g., potassium sorbate and the like), disintegration aids, or combinations thereof. See, for example, those representative components, combination of components, relative amounts of those components, and manners and methods for employing those components, set forth in U.S. Pat. No. 9,237,769 to Mua et al., U.S. Pat. No. 7,861,728 to Holton, Jr. et al., US Pat. App. Pub. No. 2010/0291245 to Gao et al., and US Pat. App. Pub. No. 2007/0062549 to Holton, Jr. et al., each of which is incorporated herein by reference. Typical inclusion ranges for such additional additives can vary depending on the nature and function of the additive and the intended effect on the final mixture, with an example range of up to about 10% by weight, based on total weight of the mixture (e.g., about 0.1 to about 5% by weight).

The aforementioned additives can be employed together (e.g., as additive formulations) or separately (e.g., individual additive components can be added at different stages involved in the preparation of the final mixture). Furthermore, the aforementioned types of additives may be encapsulated as provided in the final product or mixture. Exemplary encapsulated additives are described, for example, in WO2010/132444 to Atchley, which has been previously incorporated by reference herein.

Particles

In some embodiments, any one or more of a filler component, a tobacco material, and the overall oral product described herein can be described as a particulate material. As used herein, the term "particulate" refers to a material in the form of a plurality of individual particles, some of which can be in the form of an agglomerate of multiple particles, wherein the particles have an average length to width ratio less than 2:1, such as less than 1.5:1, such as about 1:1. In various embodiments, the particles of a particulate material can be described as substantially spherical or granular.

The particle size of a particulate material may be measured by sieve analysis. As the skilled person will readily appreciate, sieve analysis (otherwise known as a gradation test) is a method used to measure the particle size distribution of a particulate material. Typically, sieve analysis involves a nested column of sieves which comprise screens, preferably in the form of wire mesh cloths. A pre-weighed sample may be introduced into the top or uppermost sieve in the column, which has the largest screen openings or mesh size (i.e. the largest pore diameter of the sieve). Each lower sieve in the column has progressively smaller screen openings or mesh sizes than the sieve above. Typically, at the base of the column of sieves is a receiver portion to collect any particles having a particle size smaller than the screen opening size or mesh size of the bottom or lowermost sieve in the column (which has the smallest screen opening or mesh size).

In some embodiments, the column of sieves may be placed on or in a mechanical agitator. The agitator causes the vibration of each of the sieves in the column. The mechanical agitator may be activated for a pre-determined period of time in order to ensure that all particles are collected in the correct sieve. In some embodiments, the column of sieves is agitated for a period of time from 0.5 minutes to 10 minutes, such as from 1 minute to 10 minutes, such as from 1 minute to 5 minutes, such as for approximately 3 minutes. Once the agitation of the sieves in the column is complete, the material collected on each sieve is weighed. The weight of each sample on each sieve may then be divided by the total weight in order to obtain a percentage of the mass retained on each sieve. As the skilled person will readily appreciate, the screen opening sizes or mesh sizes for each sieve in the column used for sieve analysis may be selected based on the granularity or known maximum/minimum particle sizes of the sample to be analysed. In some embodiments, a column of sieves may be used for sieve analysis, wherein the column comprises from 2 to 20 sieves, such as from 5 to 15 sieves. In some embodiments, a column of sieves may be used for sieve analysis, wherein the column comprises 10 sieves. In some embodiments, the largest screen opening or mesh sizes of the sieves used for sieve analysis may be 1000 µm, such as 500 µm, such as 400 µm, such as 300 µm.

In some embodiments, any particulate material referenced herein (e.g., filler component, tobacco material, and the overall oral product) can be characterized as having at least 50% by weight of particles with a particle size as measured by sieve analysis of no greater than about 1000 µm, such as no greater than about 500 µm, such as no greater than about 400 µm, such as no greater than about 350 µm, such as no greater than about 300 µm. In some embodiments, at least 60% by weight of the particles of any particulate material referenced herein have a particle size as measured by sieve analysis of no greater than about 1000 µm, such as no greater than about 500 µm, such as no greater than about 400 µm, such as no greater than about 350 µm, such as no greater than about 300 µm. In some embodiments, at least 70% by weight of the particles of any particulate material referenced herein have a particle size as measured by sieve analysis of no greater than about 1000 µm, such as no greater than about 500 µm, such as no greater than about 400 µm, such as no greater than about 350 µm, such as no greater than about 300 µm. In some embodiments, at least 80% by weight of the particles of any particulate material referenced herein have a particle size as measured by sieve analysis of no greater than about 1000 µm, such as no greater than about 500 µm, such as no greater than about 400 µm, such as no greater than about 350 µm, such as no greater than about 300 µm. In some embodiments, at least 90% by weight of the particles of any particulate material referenced herein have a particle size as measured by sieve analysis of no greater than about 1000 µm, such as no greater than about 500 µm, such as no greater than about 400 µm, such as no greater than about 350 µm, such as no greater than about 300 µm. In some embodiments, at least 95% by weight of the particles of any particulate material referenced herein have a particle size as measured by sieve analysis of no greater than about 1000 µm, such as no greater than about 500 µm, such as no greater than about 400 µm, such as no greater than about 350 µm, such as no greater than about 300 µm. In some embodiments, at least 99% by weight of the particles of any particulate material referenced herein have a particle size as measured by sieve analysis of no greater than about 1000 µm, such as no greater than about 500 µm, such as no greater than about 400 µm, such as no greater than about 350 µm, such as no greater than about 300 µm. In some embodiments, approximately 100% by weight of the particles of any particulate material referenced herein have a particle size as measured by sieve analysis of no greater than about 1000 µm, such as no greater than about 500 µm, such as no greater than about 400 µm, such as no greater than about 350 µm, such as no greater than about 300 µm.

In some embodiments, at least 50% by weight, such as at least 60% by weight, such as at least 70% by weight, such as at least 80% by weight, such as at least 90% by weight, such as at least 95% by weight, such as at least 99% by weight of the particles of any particulate material referenced herein have a particle size as measured by sieve analysis of from about 0.01 µm to about 1000 µm, such as from about 0.05 µm to about 750 µm, such as from about 0.1 µm to about 500 µm, such as from about 0.25 µm to about 500 µm. In some embodiments, at least 50% by weight, such as at least 60% by weight, such as at least 70% by weight, such as at least 80% by weight, such as at least 90% by weight, such as at least 95% by weight, such as at least 99% by weight of the particles of any particulate material referenced herein have a particle size as measured by sieve analysis of from about 10 µm to about 400 µm, such as from about 50 µm to about 350 µm, such as from about 100 µm to about 350 µm, such as from about 200 µm to about 300 µm.

Preparation

The manner by which the various components of the present compositions are combined may vary. As such, an overall mixture of various components with e.g., powdered mixture components may be relatively uniform in nature. The components noted above, which may be in liquid or dry solid form, can be admixed in a pretreatment step prior to mixture with any remaining components of the mixture, or simply mixed together with all other liquid or dry ingredients. The various components may be contacted, combined, or mixed together using any mixing technique or equipment known in the art. Any mixing method that brings the mixture ingredients into intimate contact can be used, such as a mixing apparatus featuring an impeller or other structure capable of agitation. Examples of mixing equipment include casing drums, conditioning cylinders or drums, liquid spray apparatus, conical-type blenders, ribbon blenders, mixers available as FKM130, FKM600, FKM1200, FKM2000 and FKM3000 from Littleford Day, Inc., Plough Share types of mixer cylinders, Hobart mixers, and the like. See also, for example, the types of methodologies set forth in U.S. Pat. No. 4,148,325 to Solomon et al.; U.S. Pat. No. 6,510,855 to Korte et al.; and U.S. Pat. No. 6,834,654 to Williams, each of which is incorporated herein by reference. In some embodiments, the components forming the mixture are prepared such that the mixture thereof may be used in a starch molding process for forming the mixture. Manners and methods for formulating mixtures will be apparent to those skilled in the art. See, for example, the types of methodologies set forth in U.S. Pat. No. 4,148,325 to Solomon et al.; U.S. Pat. No. 6,510,855 to Korte et al.; and U.S. Pat. No. 6,834,654 to Williams, U.S. Pat. No. 4,725,440 to Ridgway et al., and U.S. Pat. No. 6,077,524 to Bolder et al., each of which is incorporated herein by reference.

In some embodiments, preparation of a composition or product as described herein may be useful for improving binding of an active ingredient therein. The method of preparation thus may be useful for preparing a product configured for oral use. In example embodiments, such methods can comprise mixing an active ingredient comprising charged groups with a carrier/filler component comprising oppositely charged groups such that the active ingredient is retained by the carrier/filler though bonding between the charged groups of the active ingredient with the oppositely charged of the carrier/filler component. The binding between the active ingredient and the carrier/filler can be such that said at least a portion of the active ingredient that is so-retained is configured for release from the product when the product is present in an oral cavity. In some embodiments, the methods may include functionalizing one or both of the active ingredient and the carrier/filler material to cause the active ingredient and/or the carrier/filler to have oppositely charged groups.

Configured for Oral Use

Provided herein is a product configured for oral use. The term "configured for oral use" as used herein means that the product is provided in a form such that during use, saliva in the mouth of the user causes one or more of the components of the mixture (e.g., flavoring agents and/or nicotine) to pass into the mouth of the user. In certain embodiments, the product is adapted to deliver releasable components to a user through mucous membranes in the user's mouth and, in some instances, said releasable component is an active ingredient (including, but not limited to, for example, nicotine) that can be absorbed through the mucous membranes in the mouth when the product is used.

Products configured for oral use as described herein may take various forms, including gels, pastilles, gums, lozenges, powders, and pouches. Gels can be soft or hard. Certain products configured for oral use are in the form of pastilles. As used herein, the term "pastille" refers to a dissolvable oral product made by solidifying a liquid or gel mixture so that the final product is a somewhat hardened solid gel. The rigidity of the gel is highly variable. Certain products of the disclosure are in the form of solids. Certain products can exhibit, for example, one or more of the following characteristics: crispy, granular, chewy, syrupy, pasty, fluffy, smooth, and/or creamy. In certain embodiments, the desired textural property can be selected from the group consisting of adhesiveness, cohesiveness, density, dryness, fracturability, graininess, gumminess, hardness, heaviness, moisture absorption, moisture release, mouthcoating, roughness, slipperiness, smoothness, viscosity, wetness, and combinations thereof.

The products comprising the mixtures of the present disclosure may be dissolvable. As used herein, the terms "dissolve," "dissolving," and "dissolvable" refer to mixtures having aqueous-soluble components that interact with moisture in the oral cavity and enter into solution, thereby causing gradual consumption of the product. According to one aspect, the dissolvable product is capable of lasting in the user's mouth for a given period of time until it completely dissolves. Dissolution rates can vary over a wide range, from about 1 minute or less to about 60 minutes. For example, fast release mixtures typically dissolve and/or release the active substance in about 2 minutes or less, often about 1 minute or less (e.g., about 50 seconds or less, about 40 seconds or less, about 30 seconds or less, or about 20 seconds or less). Dissolution can occur by any means, such as melting, mechanical disruption (e.g., chewing), enzymatic or other chemical degradation, or by disruption of the interaction between the components of the mixture. In some embodiments, the product can be meltable as discussed, for example, in US Patent App. Pub. No. 2012/0037175 to Cantrell et al. In other embodiments, the products do not dissolve during the product's residence in the user's mouth.

In one embodiment, the product comprising the composition of the present disclosure is in the form of a mixture disposed within a moisture-permeable container (e.g., a water-permeable pouch). Such mixtures in the water-permeable pouch format are typically used by placing one pouch containing the mixture in the mouth of a human subject/user. Generally, the pouch is placed somewhere in the oral cavity of the user, for example under the lips, in the same way as moist snuff products are generally used. The pouch preferably is not chewed or swallowed. Exposure to saliva then causes some of the components of the mixture therein (e.g., flavoring agents and/or active ingredients, such as nicotine) to pass through e.g., the water-permeable pouch and provide the user with flavor and satisfaction, and the user is not required to spit out any portion of the mixture. After about 10 minutes to about 60 minutes, typically about 15 minutes to about 45 minutes, of use/enjoyment, substantial amounts of the mixture have been ingested by the human subject, and the pouch may be removed from the mouth of the human subject for disposal.

Accordingly, in certain embodiments, the mixture as disclosed herein and any other components noted above are combined within a moisture-permeable packet or pouch that acts as a container for use of the mixture to provide a pouched product configured for oral use. Certain embodiments of the disclosure will be described with reference to the FIGURE, and these described embodiments involve snus-type products having an outer pouch and containing a mixture as described herein. As explained in greater detail below, such embodiments are provided by way of example only, and the pouched products of the present disclosure can include the composition in other forms. The mixture/construction of such packets or pouches, such as the container pouch 102 in the embodiment illustrated in the FIGURE, may be varied. Referring to the FIGURE, there is shown a first embodiment of a pouched product 100. The pouched product 100 includes a moisture-permeable container in the form of a pouch 102, which contains a material 104 comprising a composition as described herein. The pouched product 100 may be an example of a product as described herein formed at least in part from the described compositions.

Suitable packets, pouches or containers of the type used for the manufacture of smokeless tobacco products are available under the tradenames CatchDry, Ettan, General, Granit, Goteborgs Rape, Grovsnus White, Metropol Kaktus, Mocca Anis, Mocca Mint, Mocca Wintergreen, Kicks, Probe, Prince, Skruf and TreAnkrare. The mixture may be contained in pouches and packaged, in a manner and using the types of components used for the manufacture of conventional snus types of products. The pouch provides a liquid-permeable container of a type that may be considered to be similar in character to the mesh-like type of material that is used for the construction of a tea bag. Components of the mixture readily diffuse through the pouch and into the mouth of the user.

Non-limiting examples of suitable types of pouches are set forth in, for example, U.S. Pat. No. 5,167,244 to Kjerstad and U.S. Pat. No. 8,931,493 to Sebastian et al.; as well as US Patent App. Pub. Nos. 2016/0000140 to Sebastian et al.; 2016/0073689 to Sebastian et al.; 2016/0157515 to Chapman et al.; and 2016/0192703 to Sebastian et al., each of which are incorporated herein by reference. Pouches can be provided as individual pouches, or a plurality of pouches (e.g., 2, 4, 5, 10, 12, 15, 20, 25 or 30 pouches) can be connected or linked together (e.g., in an end-to-end manner) such that a single pouch or individual portion can be readily removed for use from a one-piece strand or matrix of pouches.

An example pouch may be manufactured from materials, and in such a manner, such that during use by the user, the pouch undergoes a controlled dispersion or dissolution. Such pouch materials may have the form of a mesh, screen, perforated paper, permeable fabric, or the like. For example, pouch material manufactured from a mesh-like form of rice paper, or perforated rice paper, may dissolve in the mouth of the user. As a result, the pouch and mixture each may undergo complete dispersion within the mouth of the user during normal conditions of use, and hence the pouch and mixture both may be ingested by the user. Other examples of pouch materials may be manufactured using water dispersible film forming materials (e.g., binding agents such as alginates, carboxymethylcellulose, xanthan gum, pullulan, and the like), as well as those materials in combination with materials such as ground cellulosics (e.g., fine particle size wood pulp). Preferred pouch materials, though water dispersible or dissolvable, may be designed and manufactured such that under conditions of normal use, a significant amount of the mixture contents permeate through the pouch material prior to the time that the pouch undergoes loss of its physical integrity. If desired, flavoring ingredients, disintegration aids, and other desired components, may be incorporated within, or applied to, the pouch material.

The amount of material contained within each product unit, for example, a pouch, may vary. In some embodiments, the weight of the mixture within each pouch is at least about 50 mg, for example, from about 50 mg to about 1 gram, from about 100 to 800 about mg, or from about 200 to about 700 mg. In some smaller embodiments, the weight of the mixture within each pouch may be from about 100 to about 300 mg. For a larger embodiment, the weight of the material within each pouch may be from about 300 mg to about 700 mg. If desired, other components can be contained within each pouch. For example, at least one flavored strip, piece or sheet of flavored water dispersible or water soluble material (e.g., a breath-freshening edible film type of material) may be disposed within each pouch along with or without at least one capsule. Such strips or sheets may be folded or crumpled in order to be readily incorporated within the pouch. See, for example, the types of materials and technologies set forth in U.S. Pat. No. 6,887,307 to Scott et al. and U.S. Pat. No. 6,923,981 to Leung et al.; and The EFSA Journal (2004) 85, 1-32; which are incorporated herein by reference.

A pouched product as described herein can be packaged within any suitable inner packaging material and/or outer container. See also, for example, the various types of containers for smokeless types of products that are set forth in U.S. Pat. No. 7,014,039 to Henson et al.; U.S. Pat. No. 7,537,110 to Kutsch et al.; U.S. Pat. No. 7,584,843 to Kutsch et al.; U.S. Pat. No. 8,397,945 to Gelardi et al., D592,956 to Thiellier; D594,154 to Patel et al.; and D625,178 to Bailey et al.; US Pat. Pub. Nos. 2008/0173317 to Robinson et al.; 2009/0014343 to Clark et al.; 2009/0014450 to Bjorkholm; 2009/0250360 to Bellamah et al.; 2009/0266837 to Gelardi et al.; 2009/0223989 to Gelardi; 2009/0230003 to Thiellier; 2010/0084424 to Gelardi; and 2010/0133140 to Bailey et al; 2010/0264157 to Bailey et al.; and 2011/0168712 to Bailey et al. which are incorporated herein by reference.

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:
1. An oral product comprising:
an active ingredient comprising a positively charged group; and
a filler which is carboxylated microcrystalline cellulose;

wherein the active ingredient is retained by the filler through bonding of the positively charged group and the carboxylated microcrystalline cellulose, wherein the active ingredient is configured for release when the product is present in an oral cavity.

2. The product of claim 1, wherein the active ingredient is selected from the group consisting of a nicotine component, botanicals, stimulants, amino acids, vitamins, cannabinoids, nutraceuticals, and combinations thereof.

3. The product of claim 1, wherein the active ingredient comprises protonated nicotine.

4. The product of claim 1, further comprising one or more flavoring agents.

5. The product of claim 4, wherein the one or more flavoring agents comprises a compound having a carbon-carbon double bond, a carbon-oxygen double bond, or both.

6. The product of claim 5, wherein the one or more flavoring agents comprises one or more aldehydes, ketones, esters, terpenes, terpenoids, trigeminal sensates, or a combination thereof.

7. The product of claim 5, wherein the one or more flavoring agents comprises one or more of ethyl vanillin, cinnamaldehyde, sabinene, limonene, gamma-terpinene, beta-farnesene, and citral.

8. The product of claim 1, wherein the filler is in a particulate form.

9. The product of claim 1, wherein the product comprises no more than about 10% by weight of a tobacco material, excluding any nicotine component present, based on the total weight of the mixture.

10. The product of claim 1, wherein at least the active ingredient and the filler are combined as a mixture that is enclosed in a pouch to form a pouched product, the mixture optionally being in a free-flowing particulate form.

11. The product of claim 1, wherein the product further comprises one or more salts, one or more sweeteners, one or more binding agents, one or more humectants, one or more gums, a tobacco material, a buffer, or combinations thereof.

12. The product of claim 1, wherein the positively charged group of the active ingredient comprises at least one amine group.

13. A method for improving binding of an active ingredient in an oral product, the method comprising:
mixing an active ingredient comprising a positively charged group with a filler which is carboxylated microcrystalline cellulose such that the active ingredient is retained by the filler though bonding between the positively charged group and carboxyl groups, and such that the active ingredient that is so-retained is configured for release therefrom when the product is present in an oral cavity.

14. The method of claim 13, wherein the active ingredient is selected from the group consisting of a nicotine component, botanicals, stimulants, amino acids, vitamins, cannabinoids, nutraceuticals, and combinations thereof.

15. The method of claim 14, wherein the active ingredient comprises protonated nicotine.

16. The method of claim 13, wherein the positively charged group of the active ingredient comprises at least one amine group.

* * * * *

UNITED STATES PATENT AND TRADEMARK OFFICE
CERTIFICATE OF CORRECTION

| | | |
|---|---|---|
| PATENT NO. | : 11,793,230 B2 | Page 1 of 1 |
| APPLICATION NO. | : 16/707602 | |
| DATED | : October 24, 2023 | |
| INVENTOR(S) | : Anthony Richard Gerardi et al. | |

It is certified that error appears in the above-identified patent and that said Letters Patent is hereby corrected as shown below:

On the Title Page

On page 5, in Column 1, under item (56) "Other Publications", Line 12, delete "Kskisehir," and insert -- Eskisehir, --.

Signed and Sealed this
Ninth Day of January, 2024

Katherine Kelly Vidal
*Director of the United States Patent and Trademark Office*